US007638276B2

(12) United States Patent
Griffiths et al.

(10) Patent No.: US 7,638,276 B2
(45) Date of Patent: *Dec. 29, 2009

(54) IN VITRO SORTING METHOD

(75) Inventors: Andrew Griffiths, Cambridge (GB); Dan Tawfik, Cambridge (GB)

(73) Assignee: 454 Life Sciences Corporation, Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/861,930

(22) Filed: Jun. 4, 2004

(65) Prior Publication Data
US 2005/0042648 A1 Feb. 24, 2005

Related U.S. Application Data

(60) Division of application No. 10/263,984, filed on Oct. 3, 2002, now Pat. No. 7,138,233, which is a division of application No. 09/464,122, filed on Dec. 16, 1999, now Pat. No. 6,489,103, which is a continuation of application No. PCT/GB98/01889, filed on Jun. 29, 1998.

(30) Foreign Application Priority Data

| Jul. 7, 1997 | (GB) | ................................. 9714300.2 |
| Mar. 25, 1998 | (GB) | ................................. 9806393.6 |
| Jun. 29, 1998 | (WO) | ..................... PCT/GB98/01889 |

(51) Int. Cl.
  *C12Q 1/68* (2006.01)
  *C12Q 1/66* (2006.01)
  *G01N 33/567* (2006.01)
(52) U.S. Cl. ................................. 435/6; 435/7.1; 435/8
(58) Field of Classification Search ........................ None
See application file for complete search history.

(56) References Cited

U.S. PATENT DOCUMENTS

| 4,801,529 A | | 1/1989 | Perlman ........................ 435/5 |
| 5,099,030 A | * | 3/1992 | Gardner et al. .............. 548/478 |

(Continued)

FOREIGN PATENT DOCUMENTS

DE 19646372 C1 6/1997

(Continued)

OTHER PUBLICATIONS

Lankiewicz et al., 1997, Nucleic Acid Research 25:2037-2038.*

(Continued)

*Primary Examiner*—Robert M. Kelly
*Assistant Examiner*—Kelaginamane Hiriyanna
(74) *Attorney, Agent, or Firm*—Ivor R. Elrifi, Esq.; Mintz Levin Cohn Ferris Glovsky and Popeo PC

(57) ABSTRACT

The invention describes a method for isolating one or more genetic elements encoding a gene product having a desired activity, comprising of the steps of: (a) compartmentalising genetic elements into microcapsules; (b) expressing the genetic elements to produce their respective gene products within the microcapsules; (c) sorting the genetic elements which produce the gene product having a desired activity. The invention enables the in vitro evolution of nucleic acids by repeated mutagenesis and iterative applications of the method of the invention.

11 Claims, 6 Drawing Sheets

U.S. PATENT DOCUMENTS

| | | | | |
|---|---|---|---|---|
| 5,411,876 | A | * | 5/1995 | Bloch et al. ............... 435/91.2 |
| 5,413,924 | A | | 5/1995 | Kosak et al. ................ 435/177 |
| 5,503,851 | A | | 4/1996 | Hank et al. ................. 424/489 |
| 5,508,348 | A | * | 4/1996 | Ruckenstein et al. .......... 525/98 |
| 5,516,635 | A | | 5/1996 | Ekins et al. .................... 435/6 |
| 5,518,709 | A | | 5/1996 | Sutton et al. ............... 424/9.52 |
| 5,830,663 | A | * | 11/1998 | Embleton et al. ............. 435/6 |
| 5,989,892 | A | | 11/1999 | Nishimaki et al. ........ 435/252.1 |
| 6,023,540 | A | | 2/2000 | Walt et al. ..................... 385/12 |
| 6,184,012 | B1 | | 2/2001 | Neri et al. ................... 435/188 |
| 6,258,858 | B1 | | 7/2001 | Nakajima et al. ............. 516/73 |
| 6,266,459 | B1 | | 7/2001 | Walt et al. ..................... 385/12 |
| 6,310,354 | B1 | | 10/2001 | Hänninen et al. ........ 250/458.1 |
| 6,489,103 | B1 | | 12/2002 | Griffiths et al. ................ 435/6 |
| 6,808,882 | B2 | | 10/2004 | Griffiths et al. ................ 435/6 |
| 2001/0020011 | A1 | | 9/2001 | Mathiowitz et al. ........... 514/44 |
| 2002/0022038 | A1 | | 2/2002 | Griffiths et al. ................ 435/6 |
| 2002/0119459 | A1 | | 8/2002 | Griffiths ........................ 435/6 |
| 2002/0155080 | A1 | | 10/2002 | Glenn et al. ............... 424/70.5 |
| 2003/0124586 | A1 | | 7/2003 | Griffiths et al. ................ 435/6 |
| 2004/0005594 | A1 | | 1/2004 | Holliger et al. ................ 435/6 |
| 2004/0253731 | A1 | | 12/2004 | Holliger et al. ............. 435/458 |
| 2005/0037392 | A1 | | 2/2005 | Griffiths et al. ................ 435/6 |
| 2005/0064460 | A1 | | 3/2005 | Holliger et al. ................ 435/6 |
| 2005/0079510 | A1 | | 4/2005 | Berka et al. .................... 435/6 |
| 2005/0164239 | A1 | | 7/2005 | Griffiths et al. ................ 435/6 |
| 2008/0166772 | A1 | | 7/2008 | Hollinger et al. ........... 435/91.2 |

FOREIGN PATENT DOCUMENTS

| | | |
|---|---|---|
| EP | 0 579 347 | 1/1994 |
| EP | 1 482 036 A2 | 12/2004 |
| WO | WO91/05058 | 4/1991 |
| WO | WO 93/03151 | 2/1993 |
| WO | WO 93/03151 A | 2/1993 |
| WO | WO93/08278 | 4/1993 |
| WO | WO94/16332 | 7/1994 |
| WO | WO 94/23738 A | 10/1994 |
| WO | WO94/24314 | 10/1994 |
| WO | WO 94/26766 | 11/1994 |
| WO | WO95/11922 | 5/1995 |
| WO | WO 95/24929 A | 9/1995 |
| WO | WO 96/34112 A | 10/1996 |
| WO | WO96/40723 | 12/1996 |
| WO | WO 97/40141 | 10/1997 |
| WO | WO 97/47763 | 12/1997 |
| WO | WO 98/13502 | 4/1998 |
| WO | WO 98/23733 | 6/1998 |
| WO | WO 98/31700 A | 7/1998 |
| WO | WO 98/34120 | 8/1998 |
| WO | WO98/37186 | 8/1998 |
| WO | WO 98/41869 A | 9/1998 |
| WO | WO 00/04139 | 1/2000 |
| WO | WO 00/40712 | 7/2000 |
| WO | WO 01/18244 | 3/2001 |
| WO | WO 02/22869 | 3/2002 |
| WO | WO 02/103363 | 12/2002 |
| WO | WO 03/044187 | 5/2003 |
| WO | WO 2004/069849 A2 | 8/2004 |
| WO | WO 2004/083443 A1 | 9/2004 |

OTHER PUBLICATIONS

Mattheakis, L.C. et al., (1994), "An in vitro polysome display system for identifying ligands from very large peptide libraries", *Proc. Natl. Acad. Sci. USA*, 91:9022-9026.

Cull, M.G. et al., (1992), "Screening for receptor ligands using large libraries of peptides linked to the C terminus of the *lac* repressor", *Proc. Natl. Acad. Sci. USA*, 89:1865-1869.

Clackson, T. et al., (1994), "In vitro selection from protein and peptide libraries", *Trends in Biotechnology*, 12:173-184.

Bass, S. et al., (1990), "Hormone Phage: An Enrichment Method for Variant Proteins With Altered Binding Properties", *Proteins: Structure, Function, and Genetics*, 8:309-314.

Joyce, G.F., (1994), "In vitro evolution of nucleic acids", *Structural Biology*, 4:331-336.

Chapman, K.B. et al., (1994), "In vitro selection of catalytic RNAs", *Structural Biology*, 4:618-622.

Wick, R. et al., (1996), "Enzyme-containing liposomes can endogenously produce membrane-constituting lipids", *Chemistry & Biology*, 3:277-285.

Oberholzer, T. et al., (1995), "Polymerase chain reaction in liposomes", *Chemistry & Biology*, 2:677-682.

Chakrabarti, A.C. et al., (1994), "Production of RNA by a Polymerase Protein Encapsulated Within Phospholipid Vesicles", *J. Mol. Evol*, 39:555-559.

Widersten, M. et al., (1995), "Glutathione Transferases with Novel Active Sites Isolated by Phage Display from a Library of Random Mutants", *J. Mol. Biol.*, 250:115-122.

Soumillion, P., (1994), "Selection of β13-Lactamase on Filamentous Bacteriophage by Catalytic Activity", *J. Mol. Biol.*, 237:415-422.

Oberholzer, T. et al., (1995), "Enzymatic RNA replication in self-reproducing vesicles: an approach to a minimal cell", *Biochemical and Biophysical Research Communications*, 207(1):250-257.

Keij, J.F. et al., (1994), "High-Speed Photodamage Cell Sorting: An Evaluation of the ZAPPER Prototype", *Methods in Cell Biology*, 42:371-386.

Gold, L. et al., (1995), "Diversity of Oligonucleotide Functions", *Annu. Rev. Biochem.*, 64:763-797.

Warburton, B., (1993), "Microcapsules from Multiple Emulsions", *Royal Society of Chemistry*, 138:35-51.

Tuerk, C. et al., (1990), "Systematic Evoluation of Ligands by Exponential Enrichment: RNA Ligands to Bacteriophage T4 DNA Polymerase", *Science*, 249:505-510.

Smith, G.P., (1985), "Filamentous Fusion Phage: Novel Expression Vectors That Display Cloned Antigens on the Virion Surface", *Science*, 228:1315-1317.

Green, R. et al., (1992), "Selection of a Ribozyme That Functions as a Superior Template in a Self-Copying Reaction", *Science*, 258:1910-1915.

Ellington, A.D. et al., (1990), "In Vitro selection of RNA molecules that bind specific ligands", *Nature*, 346:818-822.

McCafferty, J. et al., (1990), "Phage antibodies: filamentous phage displaying antibody variable domains", *Nature*, 348:552-554.

Moore, M.J., (1995), "Exploration by lamp light", *Nature*, 374:766-767.

Walde, P. et al., (1994), "Oparin's Reactions Revisited: Enzymatic Synthesis of Poly(adenylic acid) in Micelles and Self-Reproducing Vesicles", *J. Am. Chem. Soc.*, 116:7541-7547.

The International Search Report (PCT/GB98/01889).

Tawfik & Griffiths, (1998), "Man-Made Cell-Like Compartments for Molecular Evolution", *Nature Biotechnology*, 16: 652-656.

D.S. Tawfik, et al, (1997), "Efficient and selective p-nitrophenyl-ester-hydrolyzing antibodies elicited by a p-nitrobenzyl phosphonate hapten", *European Journal of Biochemistry*, 244: 619-626.

J. Hanes and A. Pluckthun, (1997), "In vitro selection and evolution of functional proteins by using ribosome display", *National Academy Science*, 94: 4937-4942.

Chiou et al. (2001). 'A Closed-Cycle Capillary Polymerase Chain Reaction Machine', Analytical Chemistry, American Chemical Society, 73:2018-2021.

Katsura, et al. (2001). "Indirect Micromanipulation of Single Molecules in Water-in-Oil Emulsion", Electrophoresis, 22:289-293.

Kawakatsu et al. (1997). "Regular-Sized Cell Creation in Microchannel Emulsification by Visual Microprocessing Method", Journal of the American Oil Chemists' Society, 74:317-321.

Kopp et al. (1998). "Chemical Amplification: Continuous Flow PCR on a Chip", Science, American Association for the Advancement of Science, 280:1046-1048.

Lund, et al. (1988). "Assesment of Methods for Covalent Binding of Nucleic Acids to Magnetic Beads, Dynabeads™, and the Characteristics of the Bound Nucleic Acids in Hybridization Reactions", Nucleic Acids Research, Oxford University Press, 16, No. 22, 20 pgs.

Lundeberg et al. (1995). "Solid-Phase Technology: Magnetic Beads to Improve Nucleic Acid Detection and Analysis", Biotechnology Annual Review, 1:373-401.

Nakano et al. (1994). "High Speed Polymerase Chain Reaction in Constant Flow", Bioscience Biotechnology and Biochemistry, 58:349-352.

Nakano et al. (2003). "Single-Molecule PCR Using Water-in-Oil Emulsion", Journal of Biotechnology, 102:117-124.

Park et al. (2003). "Cylindrical Compact Thermal-Cycling Device for Continuous-Flow Polymerase Chain Reaction", Analytical Chemistry, American Chemical Society, 75:6029-6033.

Russom et al. (2003). "Single-Nucleotide Polymorphism Analysis by Allele-Specific Extension of Fluorescently Labeled Nucleotides in a Microfluidic Flow-Through Device", Electrophoresis, 24:158-161.

Schneegass et al. (2001). "Miniaturized Flow-Through PCR With Different Template Types in a Silicone Chip Thermocycler", Lab on a Chip, Royal Society of Chemistry, 1:42-49.

Anarbaev et al., "Klenow fragment and DNA polymerase alpha-primase from serve calf thymus in water-in-oil emulsions", Blochimica et Biophysica Acta, 1998, pp. 315-324.

Tawfik et al., "Man-made cell-like compartments for molecular evolution", Nature Biotechnology, Jul. 1998, vol. 16, pp. 652-656.

Jun. 26, 2008 Final office Action in U.S. Appl. No. 10/866,237.

Opposition to European Patent No. EP 1 482 036 (European Patent Application No. 04077211.3) dated Jul. 2008.

Aug. 26, 2008 Amendment and Response to Feb. 27, 2008 Non-Final Office Action in U.S. Appl. No. 10/866,392.

Oct. 6, 2006 Non-Final Office Action in U.S. Appl. No. 10/866,237.

Jan. 5, 2007 Amendment and Response to Oct. 6, 2005 Non-Final Office Action in U.S. Appl. No. 10/866,237.

Mar. 27, 2007 Final Office Action in U.S. Appl. No. 10/866,237.

Jun. 25, 2007 Amendment and Response to Mar. 27, 2007 Final Office Action in U.S. Appl. No. 10/866,237.

Jul. 31, 2007 Amendment in Response to Telephonic Interview with Examiner Baughman in U.S. Appl. No. 10/866,237.

Sep. 17, 2007 Non-Final Office Action in U.S. Appl. No. 10/866,237.

Feb. 15, 2008 Amendment and Response to Sep. 17, 2007 Non-Final Office Action in U.S. Appl. No. 10/866,237.

Dec. 8, 2006 Non-Final Office Action in U.S. Appl. No. 10/865,994.

Mar. 28, 2007 Amendment and Response to Dec. 8, 2006 Non-Final Office Action in U.S. Appl. No. 10/865,994.

Jun. 19, 2007 Final Office Action in U.S. Appl. No. 10/865,994.

Aug. 7, 2007 Amendment and Response to Jun. 19, 2007 Final Office Action in U.S. Appl. No. 10/865,994.

Oct. 22, 2007 Non-Final Office Action in U.S. Appl. No. 10/865,994.

Jul. 29, 2005 Non-Final Office Action in U.S. Appl. No. 10/866,392.

Nov. 29, 2005 Amendment and Response to Jul. 29, 2005 Non-Final Office Action in U.S. Appl. No. 10/866,392.

Feb. 10, 2006 Final Office Action in U.S. Appl. No. 10/866,392.

May 2, 2006 Amendment and Response to Feb. 10, 2006 Final Office Action in U.S. Appl. No. 10/866,392.

Jun. 7, 2006 Advisory Action in U.S. Appl. No. 10/866,392.

Nov. 28, 2006 Response to Jun. 7, 2006 Advisory Action in U.S. Appl. No. 10/866,392.

Feb. 13, 2007 Non-Final Office Action in U.S. Appl. No. 10/866,392.

Jun. 14, 2007 Amendment and Response to Feb. 13, 2007 Non-Final Office Action in U.S. Appl. No. 10/866,392.

Sep. 20, 2007 Final Office Action in U.S. Appl. No. 10/866,392.

Oct. 31, 2007 Amendment and Response to Sep. 20, 2007 Final Office Action in U.S. Appl. No. 10/866,392.

Feb. 27, 2008 Non-Final Office Action in U.S. Appl. No. 10/866,392.

Anarbaev, et al. (1998). Klenow Fragment and DNA Polymerase α-Primase Fromserva Calf Thymus in Water-in-Oil Microemulsions, Biochimica et Biophysica Acta, 1384:315-324.

Atwell et al. (1999). Selection for improved Subtiligases by Phage Display, Proc. Natl. Acad. Sci. USA, 96:9497-9502.

Bauer, Johann (1999). Advances in Cell Separation: Recent Developments in Counterflow Centrifugal Elutriation and Continuous Flow Cell Separation, J. Chromotography 722:55-69.

Brody & Quake (1999). A Self-Assembled Microlensing Rotational Probe, Applied Physics Letters 74:144-146.

Demartis et al. (1999). A Strategy for the Isolation of Catalytic Activities from Repertoires of Enzymes Displayed on Phage, Academic Press Limited, Article NO. jmbi, 1998.2476, pp. 617-633.

Dressman et al. (2003). Transforming Single DNA Molecules into Fluorescent Magnetic Particles for Detection and Enumeration of Genetic Variations, PNAS 100:8817-8822.

Gašperlin et al. (2000). Viscosity Prediction of Lipophilic Semisolid Emulsion Systems by Neural Network Modelling, Int'l J. Pharrn., 196:37-50.

Gašperlin et al. (1994). The Structure Elucidation of Semisolid w/o Emulsion Systems Containing Silicone Surfactant, Int'l J. Pharm., 107:51-56.

Ghadessy et al. (2001). Directed Evolution of Polymerase Function by Compartmentalized Self-Replication, PNAS, 98:4552-57.

Griffiths & Tawflk (2003). Directed Evolution of an Extremely Fast Phosphotriesterase by in vitro Compartmentalization, EMBO J. 22:24-35.

Hsu et al. (1999). Comparison of Process Parameters for Microencapsulation of Plasmid DNA in Poly(D,L-Lactic-co-Glycolic Acid Microspheres, J. Drug Target, 7:313-23.

Janda, et al. (1997). Chemical Selection for Catalysis in Combinatorial Antibody Libraries, www.sciencemaq.orq, 275:945-948.

Jestin et al. (1999). A Method for the Selection of Catalytic Activity Using Phage Display and Proximity Coupling, Angew Chem. Int., 38:1124-1127, No. 8.

Nemoto et al. (1997). In vitro Virus: Bonding of mRNA bearing Puromycin at the 3'-Terminal End to the C-Terminal End of its Encoded Protein on the Ribosome in vitro, Federation of European BiocC46hemical Societies, pp. 405-408.

Pedersen et al. (1998). A Method for Directed Evolution and Functional Cloning of Enzymes, Proc. Natl. AC48cad. Sci. USA, 95:10523-10528.

Pelletier et al. (1C49999). An in vivo Library-versus Library Selection of Optimized Protein-Protein Interactions, Nature C50Biotechnology, 17:683-690., (1999) Nature Biotechnology.

Roberts et al. (1997). RNA-Peptide Fusions for the in vitro Selection of Peptides and Proteins, Proc. Natl. Acad. Sci. USA, 94:12297-12302.

Sepp et al. (2002). Microbead Display by in vitro Compartmentalisation: Selection for Binding Using Flow Cytometry, FEBS Letters 532:455-458.

Suzuki et al. (1996). Random Mutagenesis of Thermus Aquaticus DNA Polymerase I: Concordance of Immutable Sites in vivo with the Crystal Structure, Proc. Natl. Acad. Sci. USA, 93:9670-9675.

Vainshtein et al. (1996). Peptide Rescue of an N-Terminal Truncation of the Stoffel Fragment of Taq DNA Polymerase, Protein Science, 5:1785-1792.

Vogelstein et al. (1999). Digital PCR, Proc. Natl. Acad. Sci. USA, 96:9236-9241.

Eigen (1976). *Berichte Der Bunsen-Gesellschaft Fur Physikalische Chemie* 80: 1059-1081.

Eigen at al. (1980). *J. Theor. Biol.* 85: 407-411.

Eigen et al. (1991). *Biochemistry* 30: 11005-11018.

The European Search Report for EP 04 07 7211., Oct. 25, 2004.

Feb. 12, 2009 Non-Final Office Action in U.S. Appl. No. 12/070,232.

Summons and accompanying Communication to attend Oral Proceedings on Feb. 18, 2010 in connection with Patent Application No. 04077211.3 from the European Patent Office dated Oct. 9, 2009.

* cited by examiner

SEQUENCE LISTING

<160> NUMBER OF SEQ ID NOS: 23

<210> SEQ ID NO 1
<211> LENGTH: 60
<212> TYPE: DNA
<213> ORGANISM: Artificial
<220> FEATURE:
<223> OTHER INFORMATION: Oligonucleotide

<400> SEQUENCE: 1
agcttgcatg cctgcggtac cggccatgcg catggcctag cgcatgcggc cgctagcgcg    60

<210> SEQ ID NO 2

```
<211> LENGTH: 60
<212> TYPE: DNA
<213> ORGANISM: Artificial
<220> FEATURE:
<223> OTHER INFORMATION: Oligonucleotide

<400> SEQUENCE: 2
aattcgcgct agcggccgca tgcgctaggc catgcgcatg gccggtaccg caggcatgca    60

<210> SEQ ID NO 3
<211> LENGTH: 54
<212> TYPE: DNA
<213> ORGANISM: Artificial
<220> FEATURE:
<223> OTHER INFORMATION: Oligonucleotide

<400> SEQUENCE: 3
cgagctagag gtaccttatt aattaccttt acaaatttcc aatgcagatt ttat          54

<210> SEQ ID NO 4
<211> LENGTH: 84
<212> TYPE: DNA
<213> ORGANISM: Artificial
<220> FEATURE:
<223> OTHER INFORMATION: Oligonucleotide

<400> SEQUENCE: 4
gcatctgaca agcttaataa ttttgtttaa ctttaagaag gagatataca tatgaattta    60
attagtcttt tttcaggtgc aggg                                           84

<210> SEQ ID NO 5
<211> LENGTH: 49
<212> TYPE: DNA
<213> ORGANISM: Artificial
<220> FEATURE:
<223> OTHER INFORMATION: Oligonucleotide

<400> SEQUENCE: 5
cgagctagag gtaccttatt accgccgctc cagaatctca aagcaatag                49

<210> SEQ ID NO 6
<211> LENGTH: 82
<212> TYPE: DNA
<213> ORGANISM: Artificial
<220> FEATURE:
<223> OTHER INFORMATION: Oligonucleotide

<400> SEQUENCE: 6
gcatctgaca agcttaataa ttttgtttaa ctttaagaag gagatataca tatgatcagt    60
ctgattgcgg cgttagcggt ag                                             82

<210> SEQ ID NO 7
<211> LENGTH: 18
<212> TYPE: DNA
<213> ORGANISM: Artificial
<220> FEATURE:
<223> OTHER INFORMATION: Oligonucleotide

<400> SEQUENCE: 7
gaattggatt taggtgac                                                  18

<210> SEQ ID NO 8
<211> LENGTH: 18
<212> TYPE: DNA
<213> ORGANISM: Artificial
```

```
<220> FEATURE:
<223> OTHER INFORMATION: Oligonucleotide

<400> SEQUENCE: 8
catgattacg ccaagctc                                                18

<210> SEQ ID NO 9
<211> LENGTH: 17
<212> TYPE: DNA
<213> ORGANISM: Artificial
<220> FEATURE:
<223> OTHER INFORMATION: Oligonucleotide

<400> SEQUENCE: 9
gtaaaacgac ggccagt                                                 17

<210> SEQ ID NO 10
<211> LENGTH: 17
<212> TYPE: DNA
<213> ORGANISM: Artificial
<220> FEATURE:
<223> OTHER INFORMATION: Oligonucleotide

<400> SEQUENCE: 10
caggaaacag ctatgac                                                 17

<210> SEQ ID NO 11
<211> LENGTH: 22
<212> TYPE: DNA
<213> ORGANISM: Artificial
<220> FEATURE:
<223> OTHER INFORMATION: Oligonucleotide

<400> SEQUENCE: 11
gtctctgaat ttaccgttcc ag                                           22

<210> SEQ ID NO 12
<211> LENGTH: 22
<212> TYPE: DNA
<213> ORGANISM: Artificial
<220> FEATURE:
<223> OTHER INFORMATION: Oligonucleotide

<400> SEQUENCE: 12
gaaactgttg aaagttgttt ag                                           22

<210> SEQ ID NO 13
<211> LENGTH: 44
<212> TYPE: DNA
<213> ORGANISM: Artificial
<220> FEATURE:
<223> OTHER INFORMATION: Oligonucleotide

<400> SEQUENCE: 13
attataatac gactcactat agggagagtt atcaggcatg cacc                   44

<210> SEQ ID NO 14
<211> LENGTH: 18
<212> TYPE: DNA
<213> ORGANISM: Artificial
<220> FEATURE:
<223> OTHER INFORMATION: Oligonucleotide

<400> SEQUENCE: 14
ctagctccca ttaaggag                                                18
```

<210> SEQ ID NO 15
<211> LENGTH: 17
<212> TYPE: DNA
<213> ORGANISM: Artificial
<220> FEATURE:
<223> OTHER INFORMATION: Oligonucleotide

<400> SEQUENCE: 15
gtaaaacgac ggccagt                                                         17

<210> SEQ ID NO 16
<211> LENGTH: 17
<212> TYPE: DNA
<213> ORGANISM: Artificial
<220> FEATURE:
<223> OTHER INFORMATION: Oligonucleotide

<400> SEQUENCE: 16
caggaaacag ctatgac                                                         17

<210> SEQ ID NO 17
<211> LENGTH: 65
<212> TYPE: DNA
<213> ORGANISM: Artificial
<220> FEATURE:
<223> OTHER INFORMATION: Oligonucleotide

<400> SEQUENCE: 17
cgagctagag gtaccgcggc cgctgcgctt attaatatgg tttgaaattt aatgatgaac          60
caatg                                                                      65

<210> SEQ ID NO 18
<211> LENGTH: 83
<212> TYPE: DNA
<213> ORGANISM: Artificial
<220> FEATURE:
<223> OTHER INFORMATION: Oligonucleotide

<400> SEQUENCE: 18
gcatctgaca agcttaataa ttttgtttaa ctttaagaag gagatataca tatgattgaa          60
ataaaagata aacagctcac agg                                                  83

<210> SEQ ID NO 19
<211> LENGTH: 67
<212> TYPE: DNA
<213> ORGANISM: Artificial
<220> FEATURE:
<223> OTHER INFORMATION: Oligonucleotide

<400> SEQUENCE: 19
cgagctagag gtaccgcggc cgctgcgctt attaattacc tttacaaatt tccaatgcag          60
attttat                                                                    67

<210> SEQ ID NO 20
<211> LENGTH: 78
<212> TYPE: DNA
<213> ORGANISM: Artificial
<220> FEATURE:
<223> OTHER INFORMATION: Oligonucleotide

<400> SEQUENCE: 20
caggaaacag ctatgacaag cttaatacga ctcactatag ggagatattt tttatttttaa         60 taaggtttta attaatgg                                                        78

```
<210> SEQ ID NO 21
<211> LENGTH: 54
<212> TYPE: DNA
<213> ORGANISM: Artificial
<220> FEATURE:
<223> OTHER INFORMATION: Oligonucleotide

<400> SEQUENCE: 21
gtaaaacgac ggccagtgaa ttcttattac ttttgtaatc gtttgttttt tatc        54

<210> SEQ ID NO 22
<211> LENGTH: 77
<212> TYPE: DNA
<213> ORGANISM: Artificial
<220> FEATURE:
<223> OTHER INFORMATION: Oligonucleotide

<400> SEQUENCE: 22
caggaaacag ctatgacaag cttaatacga ctcactatag ggagaaatgg gtttctttgg  60
catatttttt acaaatg                                                 77

<210> SEQ ID NO 23
<211> LENGTH: 58
<212> TYPE: DNA
<213> ORGANISM: Artificial
<220> FEATURE:
<223> OTHER INFORMATION: Oligonucleotide

<400> SEQUENCE: 23
gtaaaacgac ggccagtgaa ttcgatatct tattactctt caattaccaa aatacccc    58
```

IN VITRO SORTING METHOD

This application is a divisional of U.S. patent application Ser. No. 10/263,984, filed on Oct. 3, 2002, now U.S. Pat. No. 7,138,233 which is a divisional of U.S. patent application Ser. No. 09/464,122, now U.S. patent Ser. No. 6,489,103, filed on Dec. 16, 1999, which is a continuation of International Application No. PCT/GB98/01889 (WO 99/02671), filed on Jun. 29, 1998, and claiming priority from British Patent Application No. 9806393.6, filed on Mar. 25, 1998, and British Patent Application No. 9714300.2, filed on Jul. 7, 1997.

The present invention relates to methods for use in vitro evolution of molecular libraries. In particular, the present invention relates to methods of selecting nucleic acids encoding gene products in which the nucleic acid and the activity of the encoded gene product are linked by compartmentation.

Evolution requires the generation of genetic diversity (diversity in nucleic acid) followed by the selection of those nucleic acids which result in beneficial characteristics. Because the nucleic acid and the activity of the encoded gene product of an organism are physically linked (the nucleic acids being confined within the cells which they encode) multiple rounds of mutation and selection can result in the progressive survival of organisms with increasing fitness. Systems for rapid evolution of nucleic acids or proteins in vitro must mimic this process at the molecular level in that the nucleic acid and the activity of the encoded gene product must be linked and the activity of the gene product must be selectable.

Recent advances in molecular biology have allowed some molecules to be co-selected according to their properties along with the nucleic acids that encode them. The selected nucleic acids can subsequently be cloned for further analysis or use, or subjected to additional rounds of mutation and selection.

Common to these methods is the establishment of large libraries of nucleic acids. Molecules having the desired characteristics (activity) can be isolated through selection regimes that select for the desired activity of the encoded gene product, such as a desired biochemical or biological activity, for example binding activity.

Phage display technology has been highly successful as providing a vehicle that allows for the selection of a displayed protein by providing the essential link between nucleic acid and the activity of the encoded gene product (Smith, 1985; Bass et al., 1990; McCafferty et al., 1990; for review see Clackson and Wells, 1994). Filamentous phage particles act as genetic display packages with proteins on the outside and the genetic elements which encode them on the inside. The tight linkage between nucleic acid and the activity of the encoded gene product is a result of the assembly of the phage within bacteria. As individual bacteria are rarely multiply infected, in most cases all the phage produced from an individual bacterium will carry the same genetic element and display the same protein.

However, phage display relies upon the creation of nucleic acid libraries in vivo in bacteria. Thus, the practical limitation on library size allowed by phage display technology is of the order of $10^7$ to $10^{11}$, even taking advantage of $\lambda$ phage vectors with excisable filamentous phage replicons. The technique has mainly been applied to selection of molecules with binding activity. A small number of proteins with catalytic activity have also been isolated using this technique, however, in no case was selection directly for the desired catalytic activity, but either for binding to a transition-state analogue (Widersten and Mannervik, 1995) or reaction with a suicide inhibitor (Soumillion et al., 1994; Janda et al., 1997).

Specific peptide ligands have been selected for binding to receptors by affinity selection using large libraries of peptides linked to the C terminus of the lac repressor LacI (Cull et al., 1992). When expressed in E. coli the repressor protein physically links the ligand to the encoding plasmid by binding to a lac operator sequence on the plasmid.

An entirely in vitro polysome display system has also been reported (Mattheakis et al., 1994) in which nascent peptides are physically attached via the ribosome to the RNA which encodes them.

However, the scope of the above systems is limited to the selection of proteins and furthermore does not allow direct selection for activities other than binding, for example catalytic or regulatory activity.

In vitro RNA selection and evolution (Ellington and Szostak, 1990), sometimes referred to as SELEX (systematic evolution of ligands by exponential enrichment) (Tuerk and Gold, 1990) allows for selection for both binding and chemical activity, but only for nucleic acids. When selection is for binding, a pool of nucleic acids is incubated with immobilised substrate. Non-binders are washed away, then the binders are released, amplified and the whole process is repeated in iterative steps to enrich for better binding sequences. This method can also be adapted to allow isolation of catalytic RNA and DNA (Green and Szostak, 1992; for reviews see Chapman and Szostak, 1994; Joyce, 1994; Gold et al., 1995; Moore, 1995).

However, selection for "catalytic" or binding activity using SELEX is only possible because the same molecule performs the dual role of carrying the genetic information and being the catalyst or binding molecule (aptamer). When selection is for "auto-catalysis" the same molecule must also perform the third role of being a substrate. Since the genetic element must play the role of both the substrate and the catalyst, selection is only possible for single turnover events. Because the "catalyst" is in this process itself modified, it is by definition not a true catalyst. Additionally, proteins may not be selected using the SELEX procedure. The range of catalysts, substrates and reactions which can be selected is therefore severely limited.

Those of the above methods that allow for iterative rounds of mutation and selection are mimicking in vitro mechanisms usually ascribed to the process of evolution: iterative variation, progressive selection for a desired the activity and replication. However, none of the methods so far developed have provided molecules of comparable diversity and functional efficacy to those that are found naturally. Additionally, there are no man-made "evolution" systems which can evolve both nucleic acids and proteins to effect the full range of biochemical and biological activities (for example, binding, catalytic and regulatory activities) and that can combine several processes leading to a desired product or activity.

There is thus a great need for an in vitro system that overcomes the limitations discussed above.

BRIEF DESCRIPTION OF THE INVENTION

According to a first aspect of the present invention, there is provided a method for isolating one or more genetic elements encoding a gene product having a desired activity, comprising the steps of:

(a) compartmentalising genetic elements into microcapsules;
(b) expressing the genetic elements to produce their respective gene products within the microcapsules;

(c) sorting the genetic elements which produce the gene product(s) having the desired activity.

The microcapsules according to the present invention compartmentalise genetic elements and gene products such that they remain physically linked together. Surprisingly, nucleic acid expression remains possible within the artificial microcapsules allowing for isolation of nucleic acid on the basis if the activity of the gene product which it encodes.

As used herein, a genetic element is a molecule or molecular construct comprising a nucleic acid. The genetic elements of the present invention may comprise any nucleic acid (for example, DNA, RNA or any analogue, natural or artificial, thereof). The nucleic acid component of the genetic element may moreover be linked, covalently or non-covalently, to one or more molecules or structures, including proteins, chemical entities and groups, solid-phase supports such as magnetic beads, and the like. In the method of the invention, these structures or molecules can be designed to assist in the sorting and/or isolation of the genetic element encoding a gene product with the desired activity.

Expression, as used herein, is used in its broadest meaning, to signify that a nucleic acid contained in the genetic element is converted into its gene product. Thus, where the nucleic acid is DNA, expression refers to the transcription of the DNA into RNA; where this RNA codes for protein, expression may also refer to the translation of the RNA into protein. Where the nucleic acid is RNA, expression may refer to the replication of this RNA into further RNA copies, the reverse transcription of the RNA into DNA and optionally the transcription of this DNA into further RNA molecule(s), as well as optionally the translation of any of the RNA species produced into protein. Preferably, therefore, expression is performed by one or more processes selected from the group consisting of transcription, reverse transcription, replication and translation.

Expression of the genetic element may thus be directed into either DNA, RNA or protein, or a nucleic acid or protein containing unnatural bases or amino acids (the gene product) within the microcapsule of the invention, so that the gene product is confined within the same microcapsule as the genetic element.

The genetic element and the gene product thereby encoded are linked by confining each genetic element and the respective gene product encoded by the genetic element within the same microcapsule. In this way the gene product in one microcapsule cannot cause a change in any other microcapsules.

The term "microcapsule" is used herein in accordance with the meaning normally assigned thereto in the art and further described hereinbelow. In essence, however, a microcapsule is an artificial compartment whose delimiting borders restrict the exchange of the components of the molecular mechanisms described herein which allow the sorting of genetic elements according to the function of the gene products which they encode.

Preferably, the microcapsules used in the method of the present invention will be capable of being produced in very large numbers, and thereby to compartmentalise a library of genetic elements which encodes a repertoire of gene products.

According to a preferred embodiment of the first aspect of the present invention, the sorting of genetic elements may be performed in one of essentially four techniques.

(I) In a first embodiment, the microcapsules are sorted according to an activity of the gene product or derivative thereof which makes the microcapsule detectable as a whole. Accordingly, the invention provides a method according to the first aspect of the invention wherein a gene product with the desired activity induces a change in the microcapsule, or a modification of one or more molecules within the microcapsule, which enables the microcapsule containing the gene product and the genetic element encoding it to be sorted. In this embodiment, therefore, the microcapsules are physically sorted from each other according to the activity of the gene product(s) expressed from the genetic element(s) contained therein, which makes it possible selectively to enrich for microcapsules containing gene products of the desired activity.

(II) In a second embodiment, the genetic elements are sorted following pooling of the microcapsules into one or more common compartments. In this embodiment, a gene product having the desired activity modifies the genetic element which encoded it (and which resides in the same microcapsule) in such a way as to make it selectable in a subsequent step. The reactions are stopped and the microcapsules are then broken so that all the contents of the individual microcapsules are pooled. Selection for the modified genetic elements enables enrichment of the genetic elements encoding the gene product(s) having the desired activity. Accordingly, the invention provides a method according to the first aspect of the invention, wherein in step (b) the gene product having the desired activity modifies the genetic element encoding it to enable the isolation of the genetic element. It is to be understood, of course, that modification may be direct, in that it is caused by the direct action of the gene product on the genetic element, or indirect, in which a series of reactions, one or more of which involve the gene product having the desired activity, leads to modification of the genetic element.

(III) In a third embodiment, the genetic elements are sorted following pooling of the microcapsules into one or more common compartments. In this embodiment, a gene with a desired activity induces a change in the microcapsule containing the gene product and the genetic element encoding it. This change, when detected, triggers the modification of the gene within the compartment. The reactions are stopped and the microcapsules are then broken so that all the contents of the individual microcapsules are pooled. Selection for the modified genetic elements enables enrichment of the genetic elements encoding the gene product(s) having the desired activity. Accordingly the invention provides a method according to the first aspect of the invention, where in step (b) the gene product having the desired activity induces a change in the compartment which is detected and triggers the modification of the genetic element within the compartment so as to allow its isolation. It is to be understood that the detected change in the compartment may be caused by the direct action of the gene product, or indirect action, in which a series of reactions, one or more of which involve the gene product having the desired activity leads to the detected change.

(IV) In a fourth embodiment, the genetic elements may be sorted by a multi-step procedure, which involves at least two steps, for example, in order to allow the exposure of the genetic elements to conditions which permit at least two separate reactions to occur. As will be apparent to a persons skilled in the art, the first microencapsulation step of the invention must result in conditions which permit the expression of the genetic elements—be it transcription, transcription and/or translation, replication or the like. Under these conditions, it may not be possible to select for a particular gene product activity, for example because the gene product may not be active under these conditions, or because the expression system contains an interfering activity. The invention therefore provides a method according to the first aspect of the present invention, wherein step (b) comprises expressing the genetic elements to produce their respective gene products within the microcapsules, linking the gene products to the genetic elements encoding them and isolating the complexes thereby formed. This allows for the genetic elements and their associated gene products to be isolated from the capsules before sorting according to gene product activity takes place. In a preferred embodiment, the complexes are subjected to a further compartmentalisation step prior to isolating the genetic elements encoding a gene product having the desired activity. This further compartmentalisation step, which advantageously takes place in microcapsules, permits the performance of further reactions, under different conditions, in an environment where the genetic elements and their respective gene products are physically linked. Eventual sorting of genetic elements may be performed according to embodiment (I), (II) or (III) above.

The "secondary encapsulation" may also be performed with genetic elements linked to gene products by other means, such as by phage display, polysome display, RNA-peptide fusion or lac repressor peptide fusion.

The selected genetic element(s) may also be subjected to subsequent, possibly more stringent rounds of sorting in iteratively repeated steps, reapplying the method of the invention either in its entirety or, in selected steps only. By tailoring the conditions appropriately, genetic elements encoding gene products having a better optimised activity may be isolated after each round of selection.

Additionally, the genetic elements isolated after a first round of sorting may be subjected to mutagenesis before repeating the sorting by iterative repetition of the steps of the method of the invention as set out above. After each round of mutagenesis, some genetic elements will have been modified in such a way that the activity of the gene products is enhanced.

Moreover, the selected genetic elements can be cloned into an expression vector to allow further characterisation of the genetic elements and their products.

In a second aspect, the invention provides a product when selected according to the first aspect of the invention. As used in this context, a "product" may refer to a gene product, selectable according to the invention, or the genetic element (or genetic information comprised therein).

In a third aspect, the invention provides a method for preparing a gene product, comprising the steps of:
 (a) preparing a genetic element encoding the gene product;
 (b) compartmentalising genetic elements into microcapsules;
 (c) expressing the genetic elements to produce their respective gene products within the microcapsules;
 (d) sorting the genetic elements which produce the gene product(s) having the desired activity; and
 (e) expressing the gene product having the desired activity.

In accordance with the third aspect, step (a) preferably comprises preparing a repertoire of genetic elements, wherein each genetic element encodes a potentially differing gene product. Repertoires may be generated by conventional techniques, such as those employed for the generation of libraries intended for selection by methods such as phage display. Gene products having the desired activity may be selected from the repertoire, according to the present invention.

In a fourth aspect, the invention provides a method for screening a compound or compounds capable of modulation the activity of a gene product, comprising the steps of:
 (a) preparing a repertoire of genetic element encoding gene product;
 (b) compartmentalising genetic elements into microcapsules;
 (c) expressing the genetic elements to produce their respective gene products within the microcapsules;
 (d) sorting the genetic elements which produce the gene product(s) having the desired activity; and
 (e) contacting a gene product having the desired activity with the compound or compounds and monitoring the modulation of an activity of the gene product by the compound or compounds.

Advantageously, the method further comprises the step of:
 (f) identifying the compound or compounds capable of modulating the activity of the gene product and synthesising said compound or compounds.

This selection system can be configured to select for RNA, DNA or protein molecules with catalytic, regulatory or binding activity.

Figure 1A:
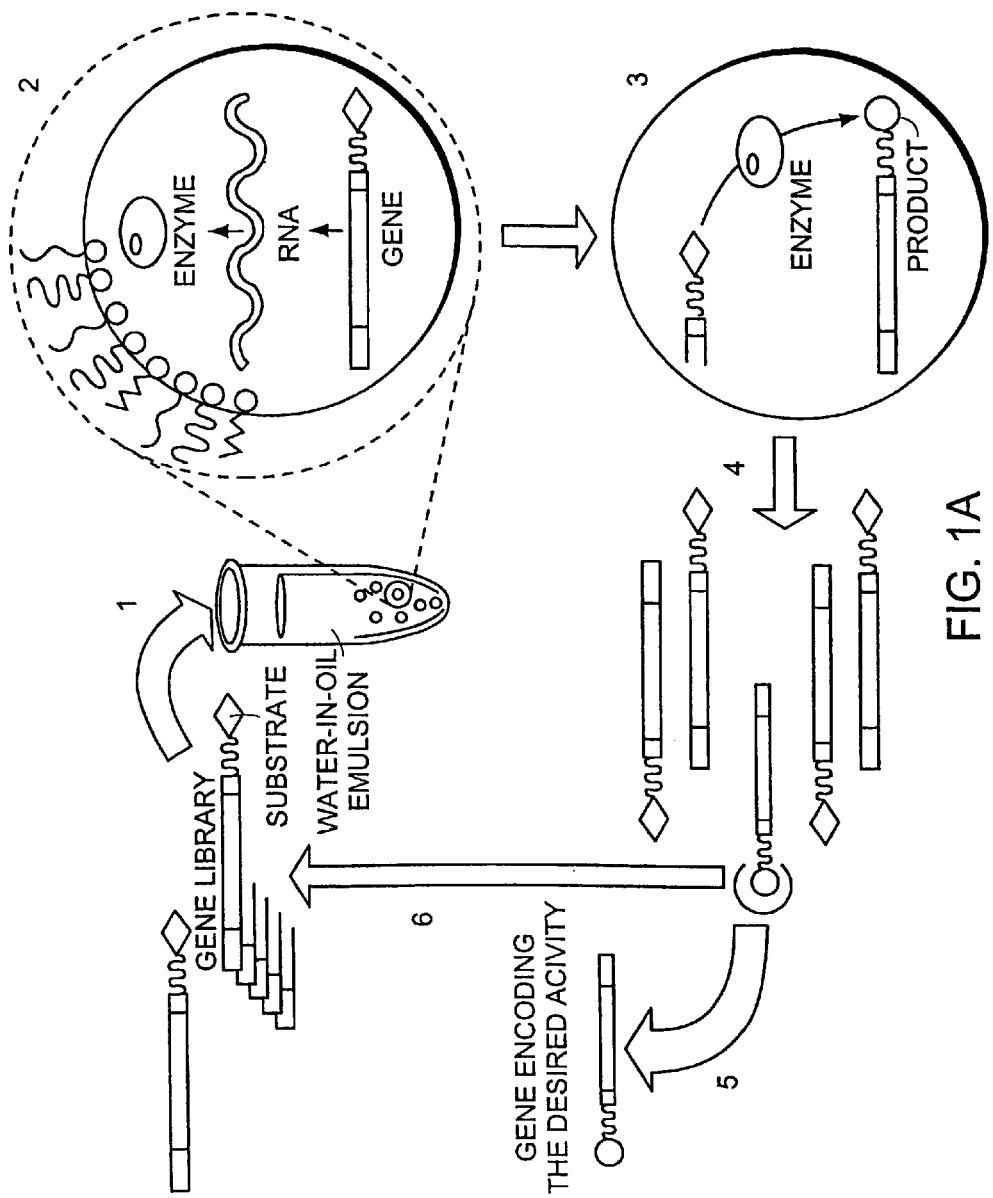
FIG. 1

Gene Selection by Compartmentalisation.

A Schematic representation of the selection procedure. In Step 1, an in vitro transcription/translation reaction mixture containing a library of genetic elements linked to a substrate for the reaction being selected is dispersed to form a water-in-oil emulsion with typically one genetic element per aqueous compartment. The genetic elements are transcribed and translated within their compartments (Step 2). Subsequently (Step 3), proteins (or RNAs) with enzymatic activities convert the substrate into a product that remains linked to the genetic element. Compartmentalisation prevents the modification of genetic elements in other compartments. Next (Step 4), the emulsion is broken, all reactions are stopped and the aqueous compartments combined. Genetic elements which are linked to the product are selectively enriched, then amplified, and either characterised (Step 5), or linked to the substrate and compartmentalised for further rounds of selection (Step 6).

B Selection for target-specific DNA methylation by HaeIII methylase. The substrate is a segment of DNA containing. HaeIII restriction/modification (R/M) sites. Genetic elements are isolated by binding to streptavidin-coated magnetic beads and treated with the cognate restriction enzyme HaeIII. Only nucleic acids with methylated R/M sites are resistant to cleavage and subsequently amplified by PCR.

FIG. 2A

Droplet size distribution and activities of DHFR and HaeIII methylase in emulsions: size distribution of the aqueous compartments in an emulsion determined by laser diffraction. In vitro transcription/translation reaction mixtures containing DNA and sodium deoxycholate are emulsified by stirring, or by stirring followed by homogenization at 8 k, 9.5 k or 13.5 k rpm. The size distribution of the aqueous particles is shown by percentage of the total aqueous volume.

FIG. 2B

The activity of DHFR formed in situ by transcription and translation of its gene (FIG. 1b) in aqueous compartments of an emulsion. The concentration of the folA gene used (2.5 nM) gives an average of one gene per droplet in the finest emulsions (homogenised at 13.5 k rpm). The mean diameter calculated from the size distribution data (in FIG. 2A) is presented as a function of the speed of homogenisation (0 k rpm refers to the emulsion prepared by stirring with no further homogenisation). Activity is presented as percentage of the activity observed in the non-emulsified in vitro reaction mixture under the same conditions.

The activity of HaeIII methylase formed in situ by transcription and translation of its gene (FIG. 1B) in aqueous compartments of an emulsion. The concentration of the M.HaeIII gene used (2.5 nM) gives an average of one gene per droplet in the finest emulsions (homogenised at 13.5 k rpm). The mean diameter calculated from the size distribution data (in FIG. 2A) is presented as a function of the speed of homogenisation; (0 k rpm refers to the emulsion prepared by stirring with no further homogenisation. Activity is presented as percentage of the activity observed in the non-emulsified in vitro reaction mixture under the same conditions.

FIG. 3

Selections for HaeIII DNA Methylase.

A Selecting M.HaeIII genes from a 1000-fold excess of folA genes. Reactions were set up with 0.2 nM of DIG-folA-3s-Biotin DNA (corresponding to an average of one gene per compartment), spiked with 0.2 pM of DIG-M.HaeIII-3s-Biotin. Reaction mixtures were either emulsified by stirring or left in solution. The DNA from these reactions was captured,digested with HaeIII (or with HhaI) and amplified by PCR. This DNA was further amplified by nested PCR with primers LMB2-Nest and LMB3-Nest and five microlitres of each nested PCR was electrophoresed on a 1.5% agarose gel containing ethidium bromide. Markers, φX174-HaeIII digest; minus T7, no T7 RNA polymerase; minus NadCh, no sodium deoxycholate.

B Two-round selections. Reactions containing a $1:10^4$ to $1:10^7$ molar ratio of DIG-M.HaeIII-3s-Biotin: DIG-folA-3s-Biotin (at 500 pM) are emulsified by stirring. The DNA from these reactions is digested with HaeIII and amplified by PCR with primers LMB2-Biotin (SEQ. ID. No. 9) and LMB3-DIG (SEQ. ID. NO. 10). The amplified DNA from the first round selection of $1:10^4$ and $1:10^5$ ratios (at 20 pM) and the $1:10^6$ and $1:10^7$ ratios (at 500 pM) is put into a second round of selection. This DNA was further amplified by nested PCR with primers LMB2-Nest and LMB3-Nest and five microlitres of nested PCR from each round of selection are analysed by gel electrophoresis as above (upper panel). The same DNA was translated in vitro and the resulting methylase activity was measured. Results are presented as the percentage of substrate DNA methylated (lower panel).

DETAILED DESCRIPTION OF THE INVENTION (A) General Description.

The microcapsules of the present invention require appropriate physical properties to allow the working of the invention.

First, to ensure that the genetic elements and gene products may not diffuse between microcapsules, the contents of each microcapsule must be isolated from the contents of the surrounding microcapsules, so that there is no or little exchange of the genetic elements and gene products between the microcapsules over the timescale of the experiment.

Second, the method of the present invention requires that there are only a limited number of genetic elements per microcapsule. This ensures that the gene product of an individual genetic element will be isolated from other genetic elements. Thus, coupling between genetic element and gene product will be highly specific. The enrichment factor is greatest with on average one or fewer genetic elements per microcapsule, the linkage between nucleic acid and the activity of the encoded gene product being as tight as is possible, since the gene product of an individual genetic element will be isolated from the products of all other genetic elements. However, even if the theoretically optimal situation of, on average, a single genetic element or less per microcapsule is not used, a ratio of 5, 10, 50, 100 or 1000 or more genetic elements per microcapsule may prove beneficial in sorting a large library. Subsequent rounds of sorting, including renewed encapsulation with differing genetic element distribution, will permit more stringent sorting of the genetic elements. Preferably, there is a single genetic element, or fewer, per microcapsule.

Third, the formation and the composition of the microcapsules must not abolish the function of the machinery the expression of the genetic elements and the activity of the gene products.

Consequently, any microencapsulation system used must fulfil these three requirements. The appropriate system(s) may vary depending on the precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

These include membrane enveloped aqueous vesicles such as lipid vesicles (liposomes) (New, 1990) and non-ionic surfactant vesicles (van Hal et al., 1996). These are closed-membranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

With a membrane-enveloped vesicle system much of the aqueous phase is outside the vesicles and is therefore non-compartmentalised. This continuous, aqueous phase should be removed or the biological systems in it inhibited or destroyed (for example, by digestion of nucleic acids with DNase or RNase) in order that the reactions are limited to the microcapsules (Luisi et al., 1987).

Enzyme-catalysed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Microcapsules can also be generated by interfacial polymerisation and interfacial complexation (Whateley, 1996). Microcapsules of this sort can have rigid, nonpermeable membranes, or semipermeable membranes. Semipermeable microcapsules bordered by cellulose nitrate membranes, polyamide membranes and lipid-polyamide membranes can all support biochemical reactions, including multienzyme systems (Chang, 1987; Chang, 1992; Lim, 1984). Alginate/polylysine microcapsules (Lim & Sun, 1980), which can be formed under very mild conditions, have also proven to be very biocompatible, providing, for example, an effective method of encapsulating living cells and tissues (Chang, 1992; Sun et al., 1992).

Non-membranous microencapsulation systems based on phase partitioning of an aqueous environment in a colloidal system, such as an emulsion, may also be used.

Preferably, the microcapsules of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

Emulsions may be produced from any suitable combination of immiscible liquids. Preferably the emulsion of the present invention has water (containing the biochemical components) as the phase present in the form of finely divided droplets (the disperse,: internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and non-ionic surfactants (Schick, 1966) such as sorbitan monooleate (Span™80; ICI) and polyoxyethylenesorbitan monooleate (Tween™ 80; ICI).

The use of anionic surfactants may also be beneficial. Suitable surfactants include sodium cholate and sodium taurocholate. Particularly preferred is sodium deoxycholate, preferably at a concentration of 0.5% w/v, or below. Inclusion of such surfactants can in some cases increase the expression of the genetic elements and/or the activity of the gene products. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalisation.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994).

Aqueous microcapsules formed in water-in-oil emulsions are generally stable with little if any exchange of genetic elements or gene products between microcapsules. Additionally, we have demonstrated that several biochemical reactions proceed in emulsion microcapsules. Moreover, complicated biochemical processes, notably gene transcription and translation are also active in emulsion microcapsules. The technology exists to create emulsions with volumes all the way up to industrial scales of thousands of litres (Becher, 1957; Sherman, 1968; Lissant, 1974; Lissant, 1984).

The preferred microcapsule size will vary depending upon the precise requirements of any individual selection process that is to be performed according to the present invention. In all cases, there will be an optimal balance between gene library size, the required enrichment and the required concentration of components in the individual microcapsules to achieve efficient expression and reactivity of the gene products.

The processes of expression must occur within each individual microcapsule provided by the present invention. Both in vitro transcription and coupled transcription-translation become less efficient at sub-nanomolar DNA concentrations. Because of the requirement for only a limited number of DNA molecules to be present in each microcapsule, this therefore sets a practical upper limit on the possible microcapsule size. Preferably, the mean volume of the microcapsules is less that $5.2 \times 10^{-16}$ m$^3$, (corresponding to a spherical microcapsule of diameter less than 10 µm, more preferably less than $6.5 \times 10^{-17}$ m$^3$ (5 µm), more preferably about $4.2 \times 10^{-18}$ m3 (2 µm) and ideally about $9 \times 10^{-18}$ m$^3$ (2.6 µm).

The effective DNA or RNA concentration in the microcapsules may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969; Blattner and Dahlberg, 1972; Roberts et al., 1975; Rosenberg et al. , 1975) , eukaryotes e. g. (Weil et al., 1979; Manley et al., 1983) and bacteriophage such as T7, T3 and SP6 (Melton et al., 1984); the polymerase chain reaction (PCR) (Saiki et al., 1988); Qβ replicase amplification (Miele et al., 1983; Cahill et al., 1991; Chetverin and Spirin, 1995; Katanaev et al., 1995); the ligase chain reaction (LCR) (Landegren et al., 1988; Barany, 1991); and self-sustained sequence replication system (Fahy et al., 1991) and strand displacement amplification (Walker et al., 1992). Even gene amplification techniques requiring thermal cycling such as PCR and LCR could be used if the emulsions and the in vitro transcription or coupled transcription-translation systems are thermostable (for example, the coupled transcription-translation systems could be made from a thermostable organism such as *Thermus aquaticus*).

Increasing the effective local nucleic acid concentration enables larger microcapsules to be used effectively. This allows a preferred practical upper limit to the microcapsule volume of about $5.2 \times 10^{-16}$ m$^3$ (corresponding to a sphere of diameter 10 µm).

The microcapsule size must be sufficiently large to accommodate all of the required components of the biochemical reactions that are needed to occur within the microcapsule. For example, in vitro, both transcription reactions and coupled transcription-translation reactions require a total nucleoside triphosphate concentration of about 2 mM.

For example, in order to transcribe a gene to a single short RNA molecule of 500 bases in length, this would require a minimum of 500 molecules of nucleoside triphosphate per microcapsule ($8.33 \times 10^{-22}$ moles). In order to constitute a 2 mM solution, this number of molecules must be contained within a microcapsule of volume $4.17 \times 10^{-19}$ litres ($4.17 \times 10^{-22}$ m$^3$ which if spherical would have a diameter of 93 nm.

Furthermore, particularly in the case of reactions involving translation, it is to be noted that the ribosomes necessary for the translation to occur are themselves approximately 20 nm in diameter. Hence, the preferred lower limit for microcapsules is a diameter of approximately 0.1 µm (100 nm).

Therefore, the microcapsule volume is preferably of the order of between $5.2 \times 10^{-22}$ m$^3$ and $5.2 \times 10^{-16}$ m$^3$ corresponding to a sphere of diameter between 0.1 µm and 10 µm, more preferably of between about $5.2 \times 10^{-19}$ m$^3$ and $6.5 \times 10^{-17}$ m$^3$ (1 µm and 5 µm). Sphere diameters of about 2.6 µm are most advantageous.

It is no coincidence that the preferred dimensions of the compartments (droplets of 2.6 μm mean diameter) closely resemble those of bacteria, for example, *Escherichia* are 1.1-1.5×2.0-6.0 μm rods and *Azotobacter* are 1.5-2.0 μm diameter ovoid cells. In its simplest form, Darwinian evolution is based on a 'one genotype one phenotype' mechanism. The concentration of a single compartmentalised gene, or genome, drops from 0.4 mM in a compartment of 2 μm diameter, to 25 pM in a compartment of 5 μm diameter. The prokaryotic transcription/translation machinery has evolved to operate in compartments of ~1-2 μm diameter, where single genes are at approximately nanomolar concentrations. A single gene, in a compartment of 2.6 μm diameter is at a concentration of 0.2 nM. This gene concentration is high enough for efficient translation. Compartmentalisation in such a volume also ensures that even if only a single molecule of the gene product is formed it is present at about 0.2 nM, which is important if the gene product is to have a modifying activity of the genetic element itself. The volume of the microcapsule should thus be selected bearing in mind not only the requirements for transcription and translation of the genetic element, but also the modifying activity required of the gene product in the method of the invention.

The size of emulsion microcapsules may be varied simply by tailoring the emulsion. conditions used to form the emulsion according to requirements of the selection system. The larger the microcapsule size, the larger is the volume that will be required to encapsulate a given genetic element library, since the ultimately limiting factor will be the size of the microcapsule and thus the number of microcapsules possible per unit volume.

The size of the microcapsules is selected not only having regard to the requirements of the transcription/translation system, but also those of the selection system employed for the genetic element. Thus, the components of the selection system, such as a chemical modification system, may require reaction volumes and/or reagent concentrations which are not optimal for transcription/translation. As set forth herein, such requirements may be accommodated by a secondary re-encapsulation step; moreover, they may be accommodated by selecting the microcapsule size in order to maximise transcription/translation and selection as a whole. Empirical determination of optimal microcapsule volume and reagent concentration, for example as set forth herein, is preferred.

A "genetic element" in accordance with the present invention is as described above. Preferably, a genetic element is a molecule or construct selected from the group consisting of a DNA molecule, an RNA molecule, a partially or wholly artificial nucleic acid molecule consisting of exclusively synthetic or a mixture of naturally-occurring and synthetic bases, any one of the foregoing linked to a polypeptide, and any one of the foregoing linked to any other molecular group or construct. Advantageously, the other molecular group or construct may be selected from the group consisting of nucleic acids, polymeric substances, particularly beads, for example polystyrene beads, magnetic substances such as magnetic beads, labels, such as fluorophores or isotopic labels, chemical reagents, binding agents such as macrocycles and the like.

The nucleic acid portion of the genetic element may comprise suitable regulatory sequences, such as those required for efficient expression of the gene product, for example promoters, enhancers, translational initiation sequences, polyadenylation sequences, splice sites and the like.

As will be apparent from the following, in many cases the polypeptide or other molecular group or construct is a ligand or a substrate which directly or indirectly binds to or reacts with the gene product in order to tag the genetic element. This allows the sorting of the genetic element on the basis of the activity of the gene product.

The ligand or substrate can be connected to the nucleic acid by a variety of means that will be apparent to those skilled in the art (see, for example, Hermanson, 1996). Any tag will suffice that allows for the subsequent selection of the genetic element. Sorting can be by any method which allows the preferential separation, amplification or survival of the tagged genetic element. Examples include selection by binding (including techniques based on magnetic separation, for example using Dynabeads™), and by resistance to degradation (for example by nucleases, including restriction endonucleases).

One way in which the nucleic acid molecule may be linked to a ligand or substrate is through biotinylation. This can be done by PCR amplification with a 5'-biotinylation primer such that the biotin and nucleic acid are covalently linked.

The ligand or substrate to be selected can be attached to the modified nucleic acid by a variety of means that will be apparent to those of skill in the art. A biotinylated nucleic acid. may be coupled to a polystyrene microbead (0.035 to 0.2 μm in diameter) that is coated with avidin or streptavidin, that will therefore bind the nucleic acid with very high affinity. This bead can be derivatised with substrate or ligand by any suitable method such as by adding biotinylated substrate or by covalent coupling.

Alternatively, a biotinylated nucleic acid may be coupled to avidin or streptavidin complexed to a large protein molecule such as thyroglobulin (669 Kd) or ferritin (440 Kd). This complex can be derivatised with substrate or ligand, for example by covalent coupling to the ε-amino group of lysines or through a non-covalent interaction such as biotin-avidin. The substrate may be present in a form unlinked to the genetic element but containing an inactive "tag" that requires a further step to activate it such as photoactivation (e.g. of a "caged" biotin analogue, (Sundberg et al., 1995; Pirrung and Huang, 1996)). The catalyst to be selected then converts the substrate to product. The "tag" could then be activated and the "tagged" substrate and/or product bound by a tag-binding molecule (e.g. avidin or streptavidin) complexed with the nucleic acid. The ratio of substrate to product attached to the nucleic acid via the "tag" will therefore reflect the ratio of the substrate and product in solution.

An alternative is to couple the nucleic acid to a product-specific antibody (or other product-specific molecule). In this scenario, the substrate (or one of the substrates) is present in each microcapsule unlinked to the genetic element, but has a molecular "tag" (for example biotin, DIG or DNP). When the catalyst to be selected converts the substrate to product, the product retains the "tag" and is then captured in the microcapsule by the product-specific antibody. In this way the genetic element only becomes associated with the "tag" when it encodes or produces an enzyme capable of converting substrate to product.

When all reactions are stopped and the microcapsules are combined, the genetic elements encoding active enzymes can be enriched using an antibody or other molecule which binds, or reacts specifically with the "tag". Although both substrates and product have the molecular tag, only the genetic elements encoding active gene product will co-purify.

The terms "isolating", "sorting" and "selecting", as well as variations thereof, are used herein. Isolation, according to the present invention, refers to the process of separating an entity from a heterogeneous population, for example a mixture, such that it is free of at least one substance with which it was associated before the isolation process. In a preferred embodiment, isolation refers to purification of an entity essentially to homogeneity. Sorting of an entity refers to the process of preferentially isolating desired entities over undesired entities. In as far as this relates to isolation of the desired entities, the terms "isolating" and "sorting" are equivalent. The method of the present invention permits the sorting of desired genetic elements from pools (libraries or repertoires) of genetic elements which contain the desired genetic element. Selecting is used to refer to the process (including the sorting process) of isolating an entity according to a particular property thereof.

In a highly preferred application, the method of the present invention is useful for sorting libraries of genetic elements. The invention accordingly provides a method according to preceding aspects of the invention, wherein the genetic elements are isolated from a library of genetic elements encoding a repertoire of gene products. Herein, the terms "library", "repertoire" and "pool" are used according to their ordinary signification in the art, such that a library of genetic elements encodes a repertoire of gene products. In general, libraries are constructed from pools of genetic elements and have properties which facilitate sorting.

Initial selection of a genetic element from a genetic element library using the present invention will in most cases require the screening of a large number of variant genetic elements. Libraries of genetic elements can be created in a variety of different ways, including the following.

Pools of naturally occurring genetic elements can be cloned from genomic DNA or cDNA (Sambrook et al., 1989); for example, phage antibody libraries, made by PCR amplification repertoires of antibody genes from immunised or unimmunised donors have proved very effective sources of functional antibody fragments (Winter et al., 1994; Hoogenboom, 1997). Libraries of genes can also be made by encoding all (see for example Smith, 1985; Parmley and Smith, 1988) or part of genes (see for example Lowman et al., 1991) or pools of genes (see for example Nissim et al., 1994) by a randomised or doped synthetic oligonucleotide. Libraries can also be made by introducing mutations into a genetic element or pool of genetic elements 'randomly' by a variety of techniques in vivo, including; using 'mutator strains', of bacteria such as *E. coli* mutD5 (Liao et al., 1986; Yamagishi et al., 1990; Low et al., 1996); using the antibody hypermutation system of B-lymphocytes (Yelamos et al., 1995). Random mutations can also be introduced both in vivo and in vitro by chemical mutagens, and ionising or UV irradiation (see Friedberg et al., 1995), or incorporation of mutagenic base analogues (Freese, 1959; Zaccolo et al., 1996). 'Random' mutations can also be introduced into genes in vitro during polymerisation for example by using error-prone polymerases (Leung et al., 1989).

Further diversification can be introduced by using homologous recombination either in vivo (see Kowalczykowski et al., 1994 or in vitro (Stemmer, 1994a; Stemmer, 1994b)).

According to a further aspect of the present invention, therefore, there is provided a method of in vitro evolution comprising the steps of:

(a) selecting one or more genetic elements from a genetic element library according to the present invention;

(b) mutating the selected genetic element(s) in order to generate a further library of genetic elements encoding a repertoire to gene products; and (c) iteratively repeating steps (a) and (b) in order to obtain a gene product with enhanced activity.

Mutations may be introduced into the genetic elements(s) as set forth above.

The genetic elements according to the invention advantageously encode enzymes, preferably of pharmacological or industrial interest, activators or inhibitors, especially of biological systems, such as cellular signal transduction mechanisms, antibodies and fragments thereof, other binding agents suitable for diagnostic and therapeutic applications. In a preferred aspect, therefore, the invention permits the identification and isolation of clinically or industrially useful products. In a further aspect of the invention, there is provided a product when isolated by the method of the invention.

The selection of suitable encapsulation conditions is desirable. Depending on the complexity and size of the library to be screened, it may be beneficial to, set up the encapsulation procedure such that 1 or less than 1 genetic element is encapsulated per microcapsule. This will provide the greatest power of resolution. Where the library is larger and/or more complex, however, this may be impracticable; it may be preferable to encapsulate several genetic elements together and rely on repeated application of the method of the invention to achieve sorting of the desired activity. A combination of encapsulation procedures may be used to obtain the desired enrichment.

Theoretical studies indicate that the larger the number of genetic element variants created the more likely it is that a molecule will be created with the properties desired (see Perelson and Oster, 1979 for a description of how this applies to repertoires of antibodies). Recently it has also been confirmed practically that larger phage-antibody repertoires do indeed give rise to more antibodies with better binding affinities than smaller repertoires (Griffiths et al., 1994). To ensure that rare variants are generated and thus are capable of being selected, a large library size is desirable. Thus, the use of optimally small microcapsules is beneficial.

The largest repertoire created to date using methods that require an in vivo step (phage-display and LacI systems) has been a $1.6 \times 10^{-11}$ clone phage-peptide library which required the fermentation of 15 litres of bacteria (Fisch et al., 1996). SELEX experiments are often carried out on very large numbers of variants (up to $10^{15}$).

Using the present invention, at a preferred microcapsule diameter of 2.6 μm, a repertoire size of at least $10^{11}$ can be selected using 1 ml aqueous phase in a 20 ml emulsion.

In addition to the genetic elements described above, the microcapsules according to the invention will comprise further components required for the sorting process to take place. Other components of the system will for example comprise those necessary for transcription and/or translation of the genetic element. These are selected for the requirements of a specific system from the following; a suitable buffer, an in vitro transcription/replication system and/or an in vitro translation system containing all the necessary ingredients, enzymes and cofactors, RNA polymerase, nucleotides, nucleic acids (natural or synthetic), transfer RNAs, ribosomes and amino acids, and the substrates of the reaction of interest in order to allow selection of the modified gene product.

A suitable buffer will be one in which all of the desired components of the biological system are active and will therefore depend upon the requirements of each specific reaction system. Buffers suitable for biological and/or chemical reactions are known in the art and recipes provided in various laboratory texts, such as Sambrook et al., 1989.

The in vitro translation system will usually comprise a cell extract, typically from bacteria (Zubay, 1973; Zubay, 1980; Lesley et al., 1991; Lesley, 1995), rabbit reticulocytes (Pelham and Jackson, 1976), or wheat germ (Anderson et al., 1983). Many suitable systems are commercially available (for example from Promega) including some which will allow coupled transcription/translation (all the bacterial systems and the reticulocyte and wheat germ TNT™ extract systems from Promega). The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected (Ellman et al., 1991; Benner, 1994; Mendel et al., 1995).

After each round of selection the enrichment of the pool of genetic elements for those encoding the molecules of interest can be assayed by non-compartmentalised in vitro transcription/replication or coupled transcription-translation reactions. The selected pool is cloned into a suitable plasmid vector and RNA or recombinant protein is produced from the individual clones for further purification and assay.

The invention moreover relates to a method for producing a gene product, once a genetic element encoding the gene product has been sorted by the method of the invention. Clearly, the genetic element itself may be directly expressed by conventional means to produce the gene product. However, alternative techniques may be employed, as will be apparent to those skilled in the art. For example, the genetic information incorporated in the gene product may be incorporated into a suitable expression vector, and expressed therefrom.

The invention also describes the use of conventional screening techniques to identify compounds which are capable of interacting with the gene products identified by the first aspect of the invention. In preferred embodiments, gene product encoding nucleic acid is incorporated into a vector, and introduced into suitable host cells to produce transformed cell lines that express the gene product. The resulting cell lines can then be produced for reproducible qualitative and/or quantitative analysis of the effect(s) of potential drugs affecting gene product function. Thus gene product expressing cells may be employed for the identification of compounds, particularly small molecular weight compounds, which modulate the function of gene product. Thus host cells expressing gene product are useful for drug screening and it is a further object of the present invention to provide a method for identifying compounds which modulate the activity of the gene product, said method comprising exposing cells containing heterologous DNA encoding gene product, wherein said cells produce functional gene product, to at least one compound or mixture of compounds or signal whose ability to modulate the activity of said gene product is sought to be determined, and thereafter monitoring said cells for changes caused by said modulation. Such an assay enables the identification of modulators, such as agonists, antagonists and allosteric modulators, of the gene product. As used herein, a compound or signal that modulates the activity of gene product refers to a compound that alters the activity of gene product in such a way that the activity of gene product is different in the presence of the compound or signal (as compared to the absence of said compound or signal).

Cell-based screening assays can be designed by constructing cell lines in which the expression of a reporter protein, i.e. an easily assayable protein, such as b galactosidase, chloramphenicol acetyltransferase (CAT) or luciferase, is dependent on gene product. Such an assay enables the detection of compounds that directly modulate gene product function, such as compounds that antagonise gene product, or compounds that inhibit or potentiate other cellular functions required for the activity of gene product.

The present invention also provides a method to exogenously affect gene product dependent processes occurring in cells. Recombinant gene product producing host cells, e.g. mammalian cells, can be contacted with a test compound, and the modulating effect(s) thereof can then be evaluated by comparing the gene product-mediated response in the presence and absence of test compound, or relating the gene product-mediated response of test cells, or control cells (i.e., cells that do not express gene product), to the presence of the compound.

In a further aspect, the invention relates to a method for optimising a production process which involves at least one step which is facilitated by a polypeptide. For example, the step may be a catalytic step, which is facilitated by an enzyme. Thus, the invention provides a method for preparing a compound or compounds comprising the steps of:

(a) providing a synthesis protocol wherein at least one step is facilitated by a polypeptide;
(b) preparing genetic elements encoding variants of the polypeptide which facilitates this step;
(c) compartmentalising the genetic elements into microcapsules;
(d) expressing the genetic elements to produce their respective gene products within the microcapsules;
(e) sorting the genetic elements which produce polypeptide gene product(s) having the desired activity; and
(f) preparing the compound or compounds using the polypeptide gene product identified in (e) to facilitate the relevant step of the synthesis.

By means of the invention, enzymes involved in the preparation of a compound may be optimised by selection for optimal activity. The procedure involves the preparation of variants of the polypeptide to be screened, which equate to a library of polypeptides as refereed to herein. The variants may be prepared in the same manner as the libraries discussed elsewhere herein.

(B) Selection Procedures

The system can be configured to select for RNA, DNA or protein gene product molecules with catalytic, regulatory or binding activity.

(i) Affinity Selection

In the case of selection for a gene product with affinity for a specific ligand the genetic element may be linked to the gene product in the mnicrocapsule via the ligand. Only gene products with affinity for the ligand will therefore bind to the genetic, element itself and therefore only genetic elements that produce active product will be retained in the selection step. In this embodiment, the genetic element will thus comprise a nucleic acid encoding the gene product linked to a ligand for the gene product.

In this embodiment, all the gene products to be selected contain a putative binding domain, which is to be selected for, and a common feature—a tag. The genetic element in each microcapsule is physically linked to the ligand. If the gene product produced from the genetic element has affinity for the ligand, it will bind to it and become physically linked to the same genetic element that encoded it, resulting in the genetic element being 'tagged'. At the end of the reaction, all of the microcapsules are combined, and all genetic elements and gene products pooled together in one environment. Genetic elements encoding gene products exhibiting the desired binding can be selected by affinity purification using a molecule that specifically binds to, or reacts specifically with, the "tag".

In an alternative embodiment, genetic elements may be sorted on the basis that the gene product, which binds to the ligand, merely hides the ligand from, for example, further binding partners. In this eventuality, the genetic element, rather than being retained during an affinity purification step, may be selectively eluted whilst other genetic elements are bound.

In an alternative embodiment, the invention provides a method according to the first aspect of the invention, wherein in step (b) the gene products bind to genetic elements encoding them. The gene products together with the attached genetic elements are then sorted as a result of binding of a ligand to gene products having the desired activity. For example, all gene products can contain an invariant region which binds covalently or non-covalently to the genetic element, and a second region which is diversified so as to generate the desired binding activity.

Sorting by affinity is dependent on the presence of two members of a binding pair in such conditions that binding may occur. Any binding pair may be used for this purpose. As used herein, the term binding pair refers to any pair of molecules capable of binding to one another. Examples of binding pairs that may be used in the present invention include an antigen and an antibody or fragment thereof capable of binding the antigen, the biotin-avidin/streptavidin pair (Savage et al., 1994), a calcium-dependent binding polypeptide and ligand thereof (e.g. calmodulin and a calmodulin-binding peptide (Stofko et al., 1992; Montigiani et at., 1996)), pairs of polypeptides which assemble to form a leucine zipper (Tripet et al., 1996), histidines (typically hexahistidine peptides) and chelated $Cu^{2+}$, $Zn^{2+}$ and $Ni^{2+}$, (e.g. Ni-NTA; Hochuli et al., 1987), RNA-binding and DNA-binding proteins (Klug, 1995) including those containing zinc-finger motifs (Klug and Schwabe, 1995) and DNA methyltransferases (Anderson, 1993), and their nucleic acid binding sites.

(ii) Catalysis

When selection is for catalysis, the genetic element in each microcapsule may comprise the substrate of the reaction. If the genetic element encodes a gene product capable of acting as a catalyst, the gene product will catalyse the conversion of the substrate into the product. Therefore, at the end of the reaction the genetic element is physically linked to the product of the catalysed reaction. When the microcapsules are combined and the reactants pooled, genetic elements encoding catalytic molecules can be enriched by selecting for any property specific to the product (FIG. 1).

For example, enrichment can be by affinity purification using a molecule (e.g. an antibody) that binds specifically to the product. Equally, the gene product may have the effect of modifying a nucleic acid component of the genetic element, for example by methylation (or demethylation) or mutation of the nucleic acid, rendering it resistant to or susceptible to attack by nucleases, such as restriction endonucleases.

Alternatively, selection may be performed indirectly by coupling a first reaction to subsequent reactions that takes place in the same microcapsule. There are two general ways in which this may be performed. First, the product of the first reaction could be reacted with, or bound by, a molecule which does not react with the substrate of the first reaction. A second, coupled reaction will only proceed in the presence of the product of the first reaction. An active genetic element can then be purified by selection for the properties of the product of the second reaction.

Alternatively, the product of the reaction being selected may be the substrate or cofactor for a second enzyme-catalysed reaction. The enzyme to catalyse the second reaction can either be translated in situ in the microcapsules or incorporated in the reaction mixture prior to microencapsulation. Only when the first reaction proceeds will the coupled enzyme generate a selectable product.

This concept of coupling can be elaborated to incorporate multiple enzymes, each using as a substrate the product of the previous reaction. This allows for selection of enzymes that will not react with an immobilised substrate. It can also be designed to give increased sensitivity by signal amplification if a product of one reaction is a catalyst or a cofactor for a second reaction or series of reactions leading to a selectable product (for example, see Johannsson and Bates, 1988; Johannsson, 1991). Furthermore an enzyme cascade system can be based on the production of an activator for an enzyme or the destruction of an enzyme inhibitor (see Mize et al., 1989). Coupling also has the advantage that a common selection system can be used for a whole group of enzymes which generate the same product and allows for the selection of complicated chemical transformations that cannot be performed in a single step.

Such a method of coupling thus enables the evolution of novel "metabolic pathways" in vitro in a stepwise fashion, selecting and improving first one step and then the next. The selection strategy is based on the final product of the pathway, so that all earlier steps can be evolved independently or sequentially without setting up a new selection system for each step of the reaction.

Expressed in an alternative manner, there is provided a method of isolating one or more genetic elements encoding a gene product having a desired catalytic activity, comprising the steps of:

(1) expressing genetic elements to give their respective gene products;
(2) allowing the gene products to catalyse conversion of a substrate to a product, which may or may not be directly selectable, in accordance with the desired activity;
(3) optionally coupling the first reaction to one or more subsequent reactions, each reaction being modulated by the product of the previous reactions, and leading to the creation of a final, selectable product;
(4) linking the selectable product of catalysis to the genetic elements by either:
   a) coupling a substrate to the genetic elements in such a way that the product remains associated with t genetic elements, or
   b) reacting or binding the selectable product to the genetic elements by way of a suitable molecular "tag" attached to the substrate which remains on the product, or
   c) coupling the selectable product (but not the substrate) to the genetic elements by means of a product-specific reaction or interaction with the product; and
(5) selecting the product of catalysis, together with the genetic element to which it is bound, either by means of a specific reaction or interaction with the product, or by affinity purification using a suitable molecular "tag" attached to the product of catalysis, wherein steps (1) to (4) each genetic element and respective gene product is contained within a microcapsule.

(iii) Regulation

A similar system can be used to select for regulatory properties of enzymes.

In the case of selection for a regulator molecule which acts as an activator or inhibitor of a biochemical process, the components of the biochemical process can either be translated in situ in each microcapsule or can be incorporated in the reaction mixture prior to microencapsulation. If the genetic element being selected is to encode an activator, selection can be performed for the product of the regulated reaction, as described above in connection with catalysis. If an inhibitor is desired, selection can be for a chemical property specific to the substrate of the regulated reaction.

There is therefore provided a method of sorting one or more genetic elements coding for a gene product exhibiting a desired regulatory activity, comprising the steps of:

(1) expressing genetic elements to give their respective gene products;
(2) allowing the gene products to activate or inhibit a biochemical reaction, or sequence of coupled reactions, in accordance with the desired activity, in such a way as to allow the generation or survival of a selectable molecule;
(3) linking the selectable molecule to the genetic elements either by
   a) having the selectable molecule, or the substrate from which it derives, attached to the genetic elements, or
   b) reacting or binding the selectable product to the genetic elements, by way of a suitable molecular "tag" attached to the substrate which remains on the product, or
   c) coupling the product of catalysis (but not the substrate) to the genetic elements, by means of a product-specific reaction or interaction with the product;
(4) selecting the selectable product, together with the genetic element to which it is bound, either by means of a specific reaction or interaction with the selectable product, or by affinity purification using a suitable molecular "tag" attached to the product of catalysis wherein steps (1) to (4) each genetic element and respective gene product is contained within a microcapsule.

(iv) Microcapsule Sorting

The invention provides for the sorting of intact microcapsules where this is enabled by the sorting techniques being employed. Microcapsules may be sorted as such when the change induced by the desired gene product either occurs or manifests itself at the surface of the microcapsule or is detectable from outside the microcapsule. The change may be caused by the direct action of the gene product, or indirect, in which a series of reactions, one or more of which involve the gene product having the desired activity leads to the change. For example, the microcapsule may be so configured that the gene product is displayed at its surface and thus accessible to reagents. Where the microcapsule is a membranous microcapsule, the gene product may be targeted or may cause the targeting of a molecule to the membrane of the microcapsule. This can be achieved, for example, by employing a membrane localisation sequence, such as those derived from membrane proteins, which will favour the incorporation of a fused or linked molecule into the microcapsule membrane. Alternatively, where the microcapsule is formed by phase partitioning such as with water-in-oil emulsions, a molecule having parts which are more soluble in the extra-capsular phase will arrange themselves such that they are present at the boundary of the microcapsule.

In a preferred aspect of the invention, however, microcapsule sorting is applied to sorting systems which rely on a change in the optical properties of the microcapsule, for example absorption or emission characteristics thereof, for example alteration in the optical properties of the mnicrocapsule resulting from a reaction leading to changes in absorbance, luminescence, phosphorescence or fluorescence associated with the microcapsule. All such properties are included in the term "optical". In such a case, microcapsules can be sorted by luminescence, fluorescence or phosphorescence activated sorting. In a highly preferred embodiment, fluorescence activated sorting is employed to sort microcapsules in which the production of a gene product having a desired activity is accompanied by the production of a fluorescent molecule in the cell. For example, the gene product itself may be fluorescent, for example a fluorescent protein such as GFP. Alternatively, the gene product may induce or modify the fluorescence of another molecule, such as by binding to it or reacting with it.

(v) Microcapsule Identification

Microcapsules may be identified by virtue of a change induced by the desired gene product which either occurs or manifests itself at the surface of the microcapsule or is detectable from the outside as described in section iii (Microcapsule Sorting). This change, when identified, is used to trigger the modification of the gene within the compartment. In a preferred aspect of the invention, microcapsule identification relies on a change in the optical properties of the microcapsule resulting from a reaction leading to luminescence, phosphorescence or fluorescence within the microcapsule. Modification of the gene within the microcapsules would be triggered by identification of luminescence, phosphorescence or fluorescence. For example, identification of luminescence, phosphorescence or fluorescence can trigger bombardment of the compartment with photons (or other particles or waves) which leads to modification of the genetic element. A similar procedure has been described previously for the rapid sorting of cells (Keij et al., 1994). Modification of the genetic element may result, for example, from coupling a molecular "tag", caged by a photolabile protecting group to the genetic elements: bombardment with photons of an appropriate wavelength leads to the removal of the cage. Afterwards, all microcapsules are combined and the genetic elements pooled together in one environment. Genetic elements encoding gene products exhibiting the desired activity can be selected by affinity purification using a molecule that specifically binds to, or reacts specifically with, the "tag".

(vi) Multi-Step Procedure

It will be also be appreciated that according to the present invention, it is not necessary for all the processes of transcription/replication and/or translation, and selection to proceed in one single step, with all reactions taking place in one microcapsule. The selection procedure may comprise two or more steps. First, transcription/replication and/or translation of each genetic element of a genetic element library may take place in a first microcapsule. Each gene product is then linked to the genetic element which encoded it (which resides in the same microcapsule). The microcapsules are then broken, and the genetic elements attached to their respective gene products optionally purified. Alternatively, genetic elements can be attached to their respective gene products using methods which do not rely on encapsulation. For example phage display (Smith, G. P., 1995), polysome display (Mattheakkis et al., 1994), RNA-peptide fusion (Roberts and Szostak, 1997) or lac repressor peptide fusion (Cull, et al., 1992).

In the second step of the procedure, each purified genetic element attached to its gene product is put into a second microcapsule containing components of the reaction to be selected. This reaction is then initiated. After completion of the reactions, the microcapsules are again broken and the modified genetic elements are selected. In the case of complicated multistep reactions in which many individual components and reaction steps are involved, one or more intervening steps may be performed between the initial step of creation and linking of gene product to genetic element, and the final step of generating the selectable change in the genetic element.

(vii) Selection by Activation of Reporter Gene Expression in Situ

The system can be configured such that the desired binding, catalytic or regulatory activity encoded by a genetic element leads, directly or indirectly to the activation of expression of a "reporter gene" that is present in all microcapsules. Only gene products with the desired activity activate expression of the reporter gene. The activity resulting from reporter gene expression allows the selection of the genetic element (or of the compartment containing it) by any of the methods described herein.

For example, activation of the reporter gene may be the result of a binding activity of the gene product in a mariner analogous to the "two hybrid system" (Fields and Song, 1989). Activation might also result from the product of a reaction catalysed by a desirable gene product. For example, the reaction product could be a transcriptional inducer of the reporter gene. For example arabinose could be used to induce transcription from the araBAD promoter. The activity of the desirable gene product could also result in the modification of a transcription factor, resulting in expression of the reporter gene. For example, if the desired gene product is a kinase or phosphatase the phosphorylation or dephosphorylation of a transcription factor may lead to activation of reporter gene expression.

(viii) Amplification

According to a further aspect of the present invention the method comprises the further step of amplifying the genetic elements. Selective amplification may be used as a means to enrich for genetic elements encoding the desired gene product.

In all the above configurations, genetic material comprised in the genetic elements may be amplified and the process repeated in iterative steps. Amplification may be by the polymerase chain reaction (Saiki et al., 1988) or by using one of a variety of other gene amplification techniques including; Qβ replicase amplification (Cahill, Foster and Mahan, 1991; Chetverin and Spirin, 1995; Katanaev, Kurnasov and Spirin, 1995); the ligase chain reaction (LCR) (Landegren et al., 1988; Barany, 1991); the self-sustained sequence replication system (Fahy, Kwoh and Gingeras, 1991) and strand displacement amplification (Walker et al., 1992).

(ix) Compartmentalisation

According to a further aspect of the present invention, there is provided a method for compartmentalising a genetic element and expressing the genetic element to form its gene product within the compartment, comprising the steps of:
  (a) forming an aqueous solution comprising the genetic element and the components necessary to express it to form its gene product;
  (b) microencapsulating the solution so as to form a discrete microcapsule comprising the genetic element; and
  (c) exposing the microcapsule to conditions suitable for the expression of the genetic element to form its gene product to proceed.

Suitable microencapsulation techniques are described in detail in the foregoing general description.

Preferably, a library of genetic elements encoding a repertoire of gene products is encapsulated by the method set forth above, and the genetic elements expressed to produce their respective gene products, in accordance with the invention. In a highly preferred embodiment, microencapsulation is achieved by forming a water-in-oil emulsion of the aqueous solution comprising the genetic elements.

The invention, accordingly, also provides a microcapsule obtainable by the method set forth above.

Various aspects and embodiments of the present invention are illustrated in the following examples. It will be appreciated-that modification of detail may be made without departing from the scope of the invention.

All documents mentioned in the text are incorporated by reference.

EXAMPLES

Example 1

The Production of Approx. 2 μm Aqueous Microcapsules in a Water-in-oil Emulsion System.

Microcapsules within the preferred size range of the present invention can be generated using a water-in-oil emulsion system.

Light white mineral oil (Sigma; M-3516) is used herein as the continuous phase and the emulsion is stabilised by emulsifiers sorbitan monooleate (Span 80, Fluka; 85548) and polyoxyethylenesorbitan monooleate (Tween 80, Sigma Ultra; P-8074) and in some cases also with 0.5% w/v sodium deoxycholate (Fluka; 30970).

The oil phase is freshly prepared by dissolving 4.5% (v/v) Span 80 (Fluka) in mineral oil (Sigma, #M-5904) followed by 0.5% (v/v) Tween 80 (SigmaUltra; #P-8074). Ice-cooled in vitro reaction mixtures (50 μl) are added gradually (in 5 aliquots of 10 μl over ~2 minutes) to 0.95 ml of ice-cooled oil-phase in a 5 ml Costar Biofreeze Vial (#2051) whilst stirring with a magnetic bar (8×3 mm with a pivot ring; Scientific Industries International, Loughborough, UK). Stirring (at 1150 rpm) is continued for an additional 1 minute on ice. In some emulsions the aqueous phase is supplemented with an anionic surfactant—e.g., sodium deoxycholate, sodium cholate, sodium glycocholate, and sodium taurocholate, typically to 0.5% (w/v).

When indicated, the emulsion is further homogenised using an Ultra-Turrax T25 disperser (IKA) equipped with an 8 mm diameter dispersing tool at 8 k, 9 k or 13.5 k rpm for 1 minute, or at 20 k rpm for 1 or 5 minutes, on ice. This reduces the microcapsule size.

The reactions may be quenched and the emulsion broken as indicated in individual examples, by spinning at 3,000 g for 5 minutes and removing the oil phase, leaving the concentrated emulsion at the bottom of the vial. Quenching buffer (typically, 0.2 ml of 25 μg/ml yeast RNA in W+B buffer: 1 M NaCl, 10 mM Tris-HCl, 1 mM EDTA pH 7.4) and 2 ml of water-saturated diethyl ether is added and the mixture vortexed, centrifuged briefly, and the ether phase removed. The aqueous phase is washed with ether and dried (5 minutes in a Speedvac at ambient temperature).

Figure 2A:
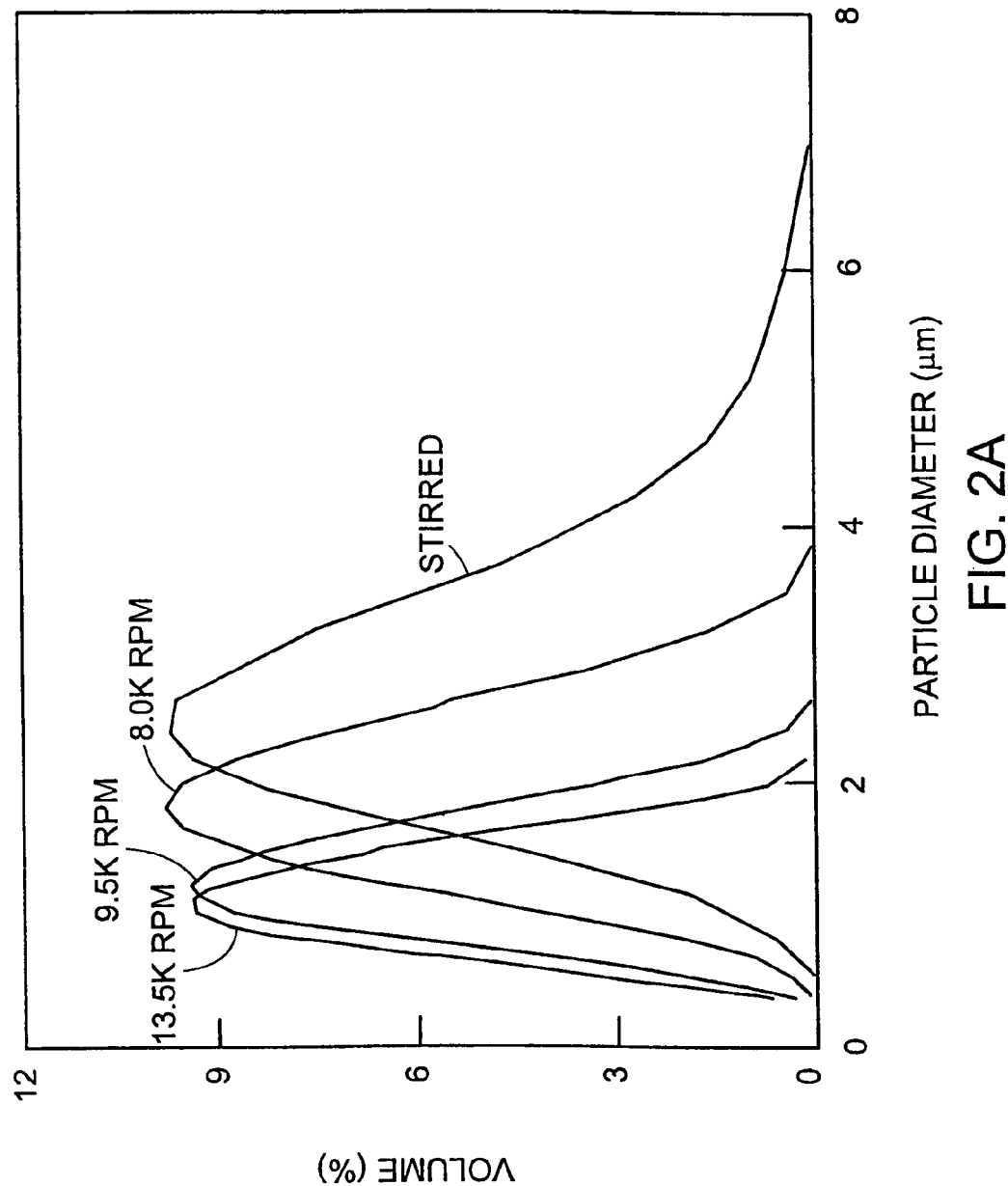
Figure 2B:
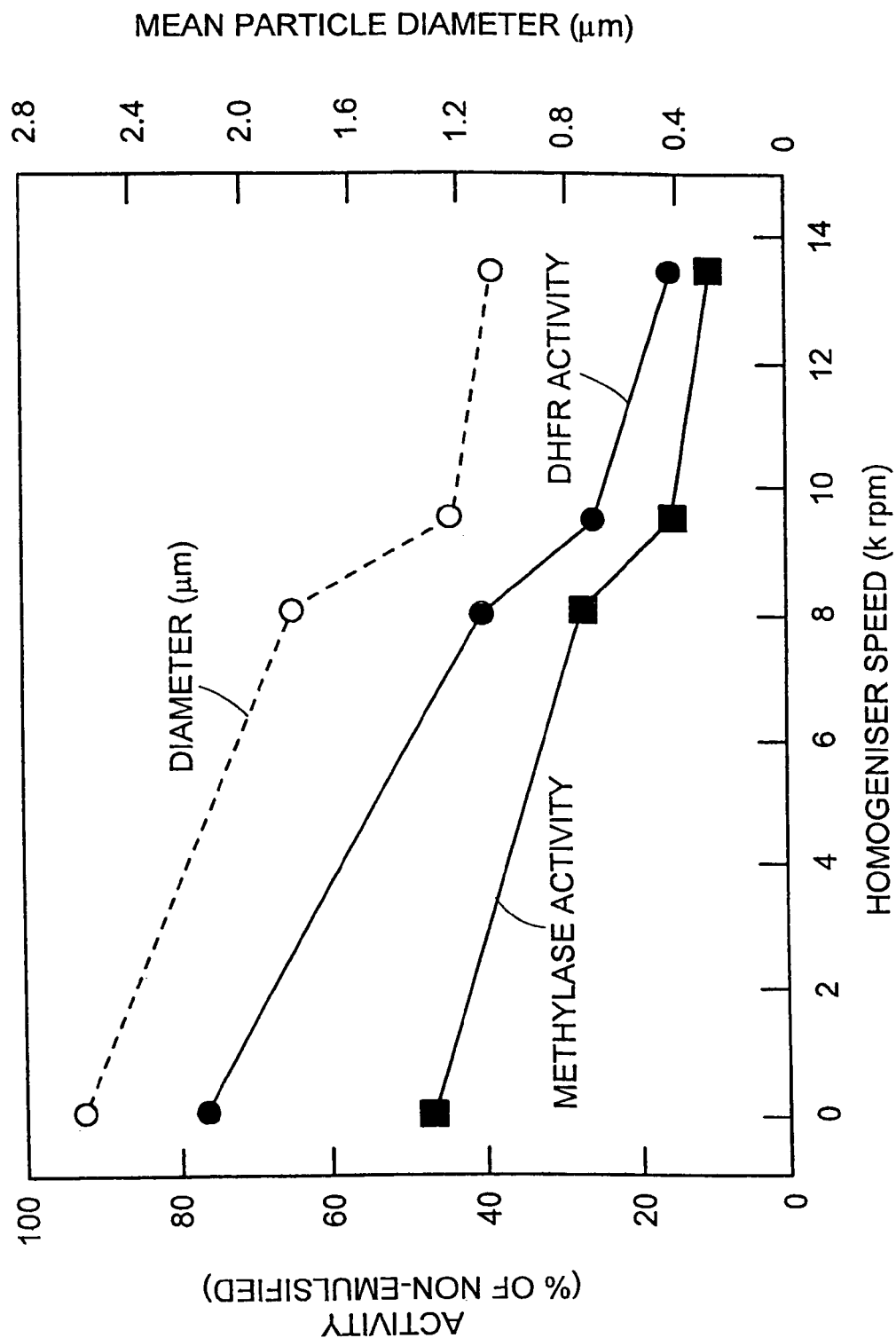

The size distribution of the aqueous droplets in the emulsions was determined by laser diffraction using a Coulter LS230 Particle Size Analyser. An aliquot of emulsion, freshly diluted (1:10) in mineral oil is added to the micro-volume chamber containing stirred mineral oil. Results are analysed with the instrument's built-in Mie optical model using refractive indices of 1.468 for mineral oil and 1.350 for the aqueous phase. The size distribution of the aqueous droplets in the emulsion is shown in FIG. 2. Addition of sodium deoxycholate does not significantly alter the size distribution.

Example 2

Efficient in vitro Transcription Reactions Performed in the Aqueous Microcapsules of a Water-in-oil Emulsion.

In order to produce RNA from DNA within each microcapsule, the single molecule of DNA present within each aqueous microcapsule of the system must be transcribed efficiently. Herein, in vitro transcription is demonstrated within microcapsules.

The catalytic core of the Tetrahymena self-splicing intron is a much-studied ribozyme which can catalyse a variety of phosphoester transfer reactions (Sag et al., 1986; Sag and Czech, 1986; Sag and Czech, 1986). For example, a modified Tetrahymena intron missing the P1 stem-loop from the 5'-end, and missing the 3'-stem-loops P9.1 and P9.2 can function as an RNA ligase, efficiently splicing together two or more oligonucleotides aligned on a template strand (Green and Szostak, 1992).

DNA encoding the above-described Tetrahymena ribozyme is PCR-amplified using primers P2T7Ba (which anneals to the P2 loop region and appends a T7 RNA polymerase promoter) and P9Fo (which anneals to the P9 loop region). This creates a 331 base pair DNA fragment carrying the T7 RNA polymerase promoter. This fragment is purified directly using Wizard PCR Preps (Promega) and used as the template for an in vitro transcription reaction using T7 RNA polymerase.

In vitro transcription is assayed over an initial 10 minute period during which the reaction rate is essentially linear (Chamberlin and Ring, 1973). Reaction conditions for transcription are as described by Wyatt et al., 1991.

Incorporation of $[\gamma^{-32}P]$ UTP is used to assay the progression of the reaction.

A transcription reaction is set up in a volume of 200 µl and divided into 2 aliquots, each containing $3\times10^{11}$ molecules of DNA (5 nM). One 100 µl aliquot is added to 2 ml Sigma light mineral oil containing 4.5% Span 80 and 0.5% Tween 80 and homogenised for 5 minutes with an Ultra-Turrax T25 disperser at 20,000 rpm as in Example 1. Based on the mean microcapsule volume in these emulsions ($2.8\times10^{-19}$ m$^3$ for a 0.81 µm diameter microcapsule) the 100 µl reaction would be divided into $3.6\times10^{11}$ microcapsules. Hence, there should be 1 molecule of DNA per microcapsule on average.

Both aliquots are incubated in a 37° C. water bath. 0.5 ml samples of the emulsion are removed both before the start of the incubation and after 10 minutes and placed on ice. Similar 25 µl samples are removed from the non-emulsified control reactions at the same time. Emulsions are broken and reactions stopped with 0.5 ml EDTA (50 mM) and 2 ml water-saturated diethyl ether as described in Example 1. 100 µl salmon sperm DNA (500 µg/ml) in 20 mM EDTA is then added. Three 100 µl aliquots are then removed from both emulsions and controls and labelled RNA is assayed by TCA precipitation and scintillation counting.

The rate of transcription is taken as the increase in acid perceptible cpm over the 10 minute incubation at 37° C. In the non emulsified control reaction there are 442,000 cpm acid perceptible material compared to 147,000 cpm in the emulsion. Hence the rate of transcription in the emulsion is 33% of that found in the non-emulsified control reaction.

This procedure therefore shows that RNA can be efficiently synthesised by T7 RNA polymerase in the aqueous microcapsules of a water-in-oil emulsion.

Example 3

Efficient Coupled in vitro Transcription/Translation Reactions Performed in the Aqueous Microcapsules of a Water-in-oil Emulsion.

In order to synthesise proteins using the procedure of the present invention, translation must be active in the aqueous microcapsules of the water-in-oil emulsion described herein.

Here it is shown how a protein (*E. coli* dihydrofolate reductase) can be efficiently produced from DNA in the aqueous microcapsules of a water-in-oil emulsion system using a coupled transcription/translation system.

The *E. coli* folA gene encoding dihydrofolate reductase (DHFR) is PCR-amplified using oligonucleotides EDHFRFo and EDHFRBa. This DNA is then cloned into the pGEM-4Z vector (Promega) digested with HindIII and KpnI downstream of the both the lac promoter and the T7 RNA polymerase promoter. The oligonucleotide EDHFRBa appends the efficient phage T7 gene 10 translational start site upstream of the DHFR start codon.

DNA sequencing identifies a clone which has the correct nucleotide sequence. Bacteria transformed with this clone (pGEM-folA) are found to over express active DHFR (driven from the lac promoter) when induced with IPTG.

The pGEM-folA plasmid is then PCR-amplified using primers LMB2 and LMB3 under the conditions described above to create a 649bp DNA fragment carrying the 7.7 RNA polymerase promoter, the phage T7 gene 10 translational start site and the folA gene. This PCR fragment is purified directly using Wizard PCR Preps (Promega) and used to program a prokaryotic in vitro coupled transcription/translation system designed for linear templates (Lesley, Brow and Burgess, 1991).

A commercial preparation of this system is used (*E. coli* S30 Extract System for Linear Templates; Promega) supplemented with T7 RNA polymerase.

A 300 µl translation reaction is set up on ice containing $3\times10^{12}$ molecules of DNA. T7 RNA polymerase ($10^4$ units) is added to drive transcription and the translated protein is labelled by the addition of $[^{35}S]$ methionine. A 150 µl aliquot of this reaction is added to 2.85 ml Sigma light mineral oil containing 4.5% Span 80 and 0.5% Tween 80 and homogenised for 1 minute with an Ultra-Turrax T25 disperser at 20,000 rpm, as in Example 1. The other aliquot is not emulsified.

Based on the mean microcapsule volume in the emulsions ($1.1\times10^{-18}$ m$^3$ for a 1.29 µm diameter microcapsule) the 150 µl reaction would be divided into $1.3\times10^{11}$, microcapsules). Hence, there should be roughly 11 molecules of DNA per microcapsule.

Four 0.5 ml aliquots are removed from the emulsion reaction mix. One aliquot is immediately put on ice and the other three are incubated in a 25° C. water bath for 2 hours before being placed on ice. Four 25 µl samples are also removed from the non-emulsified reaction mix; one is put immediately on ice and the other three are incubated in a 25° C. water bath for 2 hours and then placed on ice.

The emulsions are spun in a microfuge at 13,000 r.p.m. for 5 minutes at 4° C. and the mineral oil removed leaving the concentrated (but still intact) emulsion at the bottom of the tube. After briefly re-spinning and removing any further mineral oil, the emulsion is broken and any further translation stopped by adding 100 µl water containing 125 µg/ml puromycin, and 1 ml water saturated diethyl ether. This mixture is vortexed and respun in a microfuge at 13,000 r.p.m. for 1 minute at 4° C. The ether and dissolved mineral oil is then removed by aspiration and the extraction repeated with a further 1 ml of ether. Any remaining ether is, driven off by spinning for 5 minutes in a Speedvac at room temperature.

100 µl water containing 125 µg/ml puromycin is also added to the 25 µl non-emulsified control reactions. 25 µl of each of the samples is then precipitated with acetone and run on a 20% SDS-PAGE gel according to the instructions given by the manufacturers of the in vitro transcription/translation system (Promega). The gel is dried and scanned using a PHOSPHORIMAGER (fluorescence detection system; MOLECULAR DYNAMICS). A single strong band is seen with the expected molecular weight of DHFR (18 kd) in both the reactions performed in emulsions and in the controls. This band is accurately quantified.

In the emulsified reactions the mean area under the 18 kd peak is 15,073 units whereas the mean area under the same peak in the non-emulsified control reactions is 18,990 units. Hence, in the emulsified reactions the amount of DHFR protein is calculated to be 79% that found in the nonemulsified control reactions. This therefore indicates that the transcription/translation system is functional in the water-in-oil emulsion system of the present invention.

Example 4

Dihydrofolate Reductase Produced Using the Coupled in vitro Transcription/Translation Reactions Is Active.

Here it is shown that protein (*E. coli* dihydrofolate reductase) can be produced efficiently in a catalytically active form by coupled transcription/translation of the folA gene in the aqueous microcapsules of a water-in-oil emulsion system. In this assay, an emulsion comprising microcapsules below optimal size is used; DHFR activity is shown to be higher in the larger microcapsule sizes.

175 μl translation reactions (unlabelled) are set up on ice containing either $2 \times 10^{11}$, $6 \times 10^{12}$ or $1.8 \times 10^{12}$ molecules of the folA template DNA used in Example 3, or no DNA. T7 RNA polymerase ($6 \times 10^3$ units) are added to each reaction to drive transcription.

A 100 μl aliquot of each reaction is added to 1.9 ml Sigma flight mineral oil containing 4.5% Span 80 and 0.5% Tween 80 and homogenised for 1 minute or 5 minutes with an Ultra-Turrax T25 Homogeniser equipped with an 8 mm diameter dispersing tool, at 20,000 rpm as in Example 1. After homogenisation for 1 minute the mean diameter of particles (by volume) is 1.30 μm (median 1.28 cm). 98% b volume of the internal (aqueous) phase is present in particles varying from 0.63 μm to 2.12 μm. After homogenisation for 5 minutes the mean diameter of microcapsules (by volume) is 0.81 μm (median 0.79 μm) and 98% by volume of the internal (aqueous) phase is present in particles varying from 0.41 μm to 1.38 μM.

Based on the mean microcapsule volume in the 1 minute emulsions ($1.1 \times 10^{-18}$ m$^3$ for a 1.299 μm diameter microcapsule) the 100 μl reaction would be divided into $8.7 \times 10^{10}$ microcapsules). Hence, there should be roughly 1.3, 3.9 or 11.8 molecules of DNA per microcapsule.

Based on the mean microcapsule volume in the 5 min emulsions ($2.8 \times 10^{-19}$ M$^3$ for a 0.81 μm diameter microcapsule) the 100 μl reaction would be divided into $3.6 \times 10^{11}$ microcapsules). Hence, there should be roughly 0.3, 1.0 or 2.9 molecules of DNA per microcapsule.

The emulsions, and the non-emulsified reaction mix are incubated in a 25° C. water bath. 0.5 ml samples of the emulsion are removed immediately before the start of the incubation and after 2 hours and placed on ice. 25 μl samples are removed from the non-emulsified control reactions at the same times.

The emulsions are spun in a microfuge at 13,000 r.p.m. for 5 min. at 4° C. and the mineral oil removed by aspiration, leaving the concentrated (but still intact) emulsion at the bottom of the tube. After briefly re-spinning and removing any further mineral oil the emulsion is broken and any further translation stopped by adding 100 μl Buffer A (100 mM Imidazole pH 7.0, 10; mM β-mercaptoethanol), containing 125 μg/ml puromycin and 1 ml water saturated diethyl ether. The mixture is vortexed and spun in a microfuge at 13,000 r.p.m. for 1 min. at 40° C. The ether and dissolved mineral oil is removed by aspiration and the extraction repeated with a further 1 ml of ether. Any remaining ether is driven off by spinning for 5 minutes in a Speedvac at room temperature. 100 μl Buffer A containing (125 μg/ml) puromycin is also added to the 25 μl non-emulsified control reactions.

Dihydrofolate reductase activity is assayed as by spectrophotometrically monitoring the oxidation of NADPH to NADP at 340 nm over a 10 minute time course as described by Williams et al., 1979; Ma et al., 1993. 10 μl of each quenched in vitro translation reaction is added to 150 μl Buffer A (100 mM Imidazole, pH 7.0, 10 mM β-mercaptoethanol) and 20 μl 1 mM NADPH. 20 μl Dihydrofolate (1 mM)(H$_2$F) is added after 1 minute and the reaction monitored at 340 nm using a ThermoMax microplate reader (Molecular Devices). Activity is calculated by initial velocities under So$>>$K$_M$ conditions ($\upsilon_{max}$). The background activity in the S30 extract is subtracted from all samples.

DHFR activity generated in the emulsions is taken from the difference in activity measured at 0 hours and 2 hours incubation. No increase in NADPH oxidation occurred between the 0 hour and 2 hour samples when 0.1 μM methotrexate (a specific inhibitor of DHFR) is added showing that all the increase in NADPH oxidation observed is due to DHFR produced in the in vitro translation reactions.

Using 1 minute homogenisation at 20,000 rpm, the DHFR activity generated in the emulsions is 31% that found in the non-emulsified control reactions with 1.3 molecules of DNA per microcapsule; 45% with 3.9 molecules of DNA per microcapsule; and 84% with 11.8 molecules of DNA per microcapsule.

Using 5 minute homogenisation at 20,000 rpm, the DHFR activity generated in the emulsions is 7% that found in the non-emulsified control reactions with 0.3 molecules of DNA per microcapsule; 15% with 1 molecule of DNA per microcapsule; and 35% with 2.9 molecules of DNA per microcapsule, on average.

Assuming the turnover number of DHFR is as described by Posner et al., 1996, this corresponds to a yield at the highest DNA concentration of 6.3 μg (340 pmole) DHFR per 100 μl reaction (non-emulsified control), 1.98 μg (104 pmole) DHFR per 100 μl reaction (emulsified for 1 min), or 0.46 μg (24.8 pmole) per 100 μl reaction (emulsified for 5 minutes). This equates to 74 molecules DHFR per microcapsule in the 1 minute emulsions and 44 molecules per microcapsule in the 5 minute emulsions (assuring that all microcapsules are of mean size).

The DHFR activity resulting from coupled transcription/translation of folA genes is also measured in the larger microcapsules produced by stirring alone, or by stirring followed by further homogenisation with an Ultra-Turrax T25 disperser at 8,000 rpm, 9,000 rpm, or 13,500 rpm for 1 minute as described in Example 1. The results are presented in FIG. 2b. The concentration of folA genes used (2.5 nM) gives an average of 1, 1.5 and 4.8 genetic elements per droplet in the emulsions homogenised at 13,500 rpm, 9,500 rpm and 8,000 rpm, respectively, and an average of 14 genetic element per droplet in the emulsion prepared by stirring only. Addition of sodium deoxycholate (0.5%) to the in vitro translation reaction mixture does not significantly affect the DHFR activity observed in the broken emulsions.

Example 5

Linkage of an Immobilised Substrate into a Genetic Element via a High Molecular Weight Protein.

In order to link multiple immobilised substrate molecules to a DNA fragment comprising the folA gene, the DNA fragment is first biotinylated and then coupled to a complex of avidin with apoferritin. Horse spleen apoferritin is a large, near spherical protein molecule of 12.5 nm diameter which therefore provides multiple sites which can be derivatised with substrate (e.g. the ε-amino group of surface lysines). The pGEM-folA plasmid encoding *E. coli* DHFR is PCR amplified using the primers LMB3 and 5'-biotinylated LMB2 (LMB2-Biotin) to create a biotinylated 649bp DNA fragment carrying the T7 RNA polymerase promoter, the phage T7 gene 10 translational start site and the folA gene (see Example 3). The DNA is radiolabelled by supplementing the 500 µl PCR reaction mix with 100 µCi [α-$^{32}$P]dCTP (Amersham; 3000 Ci/mmol). The biotinylated PCR fragment is purified directly using Wizard PCR Preps (Promega) and the concentration determined spectrophotometrically. The percentage of DNA biotinylated is assayed by binding to Streptavidin M-280 DYNABEADS (superparamagnetic particles; Dynal) and scintillation counting. 83% of the DNA is determined to be biotinylated using this technique.

The sequestered iron is removed from a commercial conjugate of avidin and ferritin (Avidin-Ferritin; approx. 1.1 mole ferritin per mole avidin; Sigma) by the overnight dialysis (4° C.) of a solution of avidin-ferritin in PBS (1 mg/ml) against 0.12M thioglycollic acid, pH 4.25, followed by 24 hours dialysis against PBS (4° C.) as described by Kadir and Moore, 1990. Removal of iron is checked by analysis of the absorbance spectra (sequestered Fe(III) absorbs strongly at 310-360 nm).

0.3 pmole radiolabelled, biotinylated DNA is incubated with varying molar ratios of avidin-apoferritin in PBS (total volume 9 µl) for 30 minutes at room temperature. A 4.5 µl aliquot is removed and the percentage of DNA complexed with avidin-apoferritin assayed using and-shifting assay on a 1.5% agarose gel as described by Berman et al., 1987. The gel is then dried and scanned using a PHOSPHORIMAGER (fluorescence detection system; MOLECULAR DYNAMICS). The percentage of DNA remaining unshifted (i.e. not complexed with avidin-apoferritin) is 17% (1:1 molar ratio avidin- apoferritin:DNA), 15% (5:1 molar ratio avidin-apoferritin:DNA) or 14% (25:1 molar ratio avidin-apoferritin:DNA). This means that even at a 1:1 ratio of avidin-apoferritin:DNA basically all the biotinylated DNA is bound. No band-shifting is observed when biotinylated DNA is mixed with apoferritin or when non-biotinylated DNA is mixed with avidin-apoferritin.

The remaining 4.5 µl of DNA complexed with avidin-apoferritin is used as the template for a 25 µl in vitro transcription/translation reaction (*E. coli* S30 Extract System for Linear Templates; Promega). After 2 hours at 25° C., the reaction is stopped by adding 100 µl Buffer A containing puromycin (125 µg/ml). Dihydrofolate reductase activity is assayed as above by spectrophotometrically monitoring the oxidation of NADPH to NADP at 340 nm over a 10 minute time course.

10 µl of each in vitro translation reaction is added to 150 µl Buffer A and 20 µl NADPH (1 mM). 20 µl Dihydrofolate (1 mM) (Emulsions were broken and reactions were stopped with 0.5 ml EDTA (50 mM) and 2 ml water-saturated diethyl ether as described in Example 1) is added after 1 minute and the reaction monitored at 340 nm using a ThermoMax microplate reader (Molecular Devices). No difference in DHFR activity is found at even the highest ratio avidin-apoferritin:DNA compared to a control with no avidin-apoferritin added. This indicates that the vast majority of DNA can be complexed without compromising the efficiency of in vitro translation.

Example 6

Both in vitro Transcription-translation and DHFR Activity Are Compatible in the Same System.

In order to select for the activity of DHFR produced in situ by coupled transcription-translation both the transcription-translation reaction and DHFR must be active in the same buffer system.

A direct assay for DHPR activity in a complete *E. coli* in vitro translation system based on the spectrophotometrically monitoring of the oxidation of NADPH to NADP at 340 nm is not practical due to the turbidity of the S30 extracts.

However, it is possible to ascertain that DHFR is active in the same buffer system as in vitro translation. *E. coli* DHFR is obtained by IPTG-induction of bacteria containing the plasmid pGEM-folA and affinity-purified on a methotrexate-Sepharose column (Baccanari et al., 1977).

DHFR activity is compared in Buffer A as above or in an in vitro translation mixture complete except for the substitution of S30 dialysis buffer (Lesley 1995) (10 mM Tris-acetate pH8.0, 14 mM magnesium acetate, 60 nM potassium acetate, 1 mM DTT) for the S30 fraction. In each case the total reaction volume is 200 µl and the concentration of NADPH and Emulsions were broken and reactions were stopped with 0.5 ml EDTA (50 mM) and 2 ml water-saturated diethyl ether as described in Example 1 each 0.1 mM. Reactions are monitored spectrophotometrically at 340 nm. Addition of 1.75 pmole (1.3 mUnits) *E. coli* DHFR gives initial rates of −25.77 mOD/min (in Buffer A) and −11.24 mOD/min (in translation buffer), hence the reaction is 44% as efficient in the translation buffer as in an optimised buffer (buffer A).

Furthermore, the presence of the substrates of DHFR (NADPH and $H_2F$) at 0.1 mM concentration (either alone or in combination) does not cause any inhibition of the production of active DHFR from a 2 hour coupled transcription-translation reaction.

Example 7

The Activity of DHFR on a Genetic Element Containing an Immobilised Dihydrofolate Substrate Leads to the Formation of a Tetrahydrofolate Product Linked to Nucleic Acid Encoding DHFR.

A peptide is synthesised comprising three glutamic acids linked via their γ-caboxylates (using N-fluorenylmethoxycarbonyl-glutamic acid α-benzyl ester as a starting material) with a lysine at the carboxy-terminus and biotia linked to its ε-amino group by modifying published procedures (Krumdiek et al., 1980). Folic acid is linked at the amino-terminus and the benzyl and trifluoroacetamide protective groups removed by alkaline hydrolysis as previously described. The peptide is purified by reverse phase HPLC and characterised by mass and UV spectroscopy. This folic acid peptide is chemically reduced to the corresponding dihydrofolic acid peptide (using dithionate and ascorbic acid) and then to the corresponding tetrahydrofolic acid peptide (using sodium borohydride) by applying published procedures (Zakrzewski et al., 1980). These transformations are characterised by UV spectroscopy.

A genetic element is constructed by linking, on average, two to three molecules of the folic acid peptide to avidin (or streptavidin) together with one molecule of the DHFR encoding, PCR-amplified DNA from the plasmid pGEM-folA using primers LMB2-Biotin (SEQ. ID. No. 9) and LMB3 (see Example 3). The immobilised folic acid is chemically reduced to dihydrofolate using dithionate and ascorbic acid and purified by dialysis against buffer A. E. coli DHPR is obtained by IPTG induction of bacteria containing the plasmid. pGEM-folA and affinity purified on a methotrexate-Sepharose column. E. coli DHFR is shown to react with the dihydrofolic acid immobilised to this genetic element by monitoring the oxidation of NADPH to NADP spectrophotometrically using 0-10 µM of the avidin-linked dihydrofolic acid peptide and 0-50 µM NADPH. Hence, at the end of this reaction, the product tetrahydrofolate is linked to the folA gene which encodes for the enzyme (i.e., DHFR) that catalyses its formation.

To isolate those genes attached to the tetrahydrofolate product there are two approaches. The first involves the generation of phage-display antibodies specific for tetrahydrofolate (Hoogenboom, 1997). The second approach is based on the use of a tagged reagent which reacts specifically with the immobilised product, but not with the substrate. We have synthesised a molecule consisting of a dinitrophenyl (DNP) tag linked to benzaldehyde via a 14 atom spacer. The aldehyde group reacts specifically with tetrahydrofolate to form a covalent adduct (Kallen and Jencks, 1966) and affinity purification can be performed using an anti-DNP antibody.

Example 8

An Alternative Method of Selecting for DHFR Activity

The DHFR-catalysed reaction can be selected for by in situ coupling to a second reaction, catalysed by Yeast Aldehyde Dehydrogenase, with a 'tagged' substrate.

Instead of selecting for genes connected to one of the products of the DHFR reaction (5,6,7,8-tetrahydrofolate or $NADP^+$) the DHFR reaction is coupled to a second reaction. Selection is in this case is mediated by the formation of the second product of the DHFR-catalysed reaction—nicotinamide adenine dinucleotide phosphate ($NADP^+$).

The reaction we have chosen to couple is catalysed by Yeast Aldehyde Dehydrogenase (YAD; EC 1.2.1.5). This enzyme uses either $NAD^+$ or $NADP^+$ in the oxidation of a wide range of aliphatic and aromatic aldehydes to their corresponding carboxylic acids, generating NADH or NADPH in the process. The reaction has the big advantage of being essentially irreversible—namely, dehydrogenases (including DHFR and YAD) do not catalyse the reduction of the acid back to the aldehyde. Since a large number of enzymes catalysing redox reactions generate $NAD^+$ or $NADP^+$ the YAD reaction can be used in the selection of these enzymes too, and is not limited solely to selection for Dihydrofolate Reductase.

A pentaldehyde substrate is synthesised and linked to a DNP (dinitrophenyl) tag via a $C_{20}$ linker (hereafter, DNP-PA). The oxidation of DNP-PA to the corresponding acid (DNP-PC) is followed and by HPLC (reverse phase $C_{18}$ column; $H_2O/CH_3CN$ gradient+0.1% trifluoroacetic acid; retention times: DNP-PA, 5.0 mins; DNP-PC, 4.26 mins). Conversion of DNP-PA to DNP-PC is observed only in the presence of both YAD and $NADP^+$. Reactions are also followed spectrophotometrically; the increase of absorbance at 340 nm indicated that $NADP^+$ is simultaneously converted to NADPH.

The coupled DHFR-YAD reaction is followed using the same HPLC assay. The initial reaction mixture contained the substrates for DHFR-NADPH (50 µM) and 7-8-dihydrofolate ($H_2F$; 50 µM), YAD (Sigma, 0.5 unit) and DNP-PA (50 µM) in buffer pH 7.7 (100 mM imidazole, 5 mM β-mercaptoethanol and 25 mM KCl). Conversion of DNP-PA to DNP-PC is observed when DHFR is added to the above reaction mixture (DHFR 5 nM, 83%; 1.25 nM, 14.5% after 32 mins).

The concentration of DHFR-obtained-in the compartmentalised in vitro translation is in fact much higher than 5 nM (see Example 4). The conversion of DNP-PA to DNP-PC is negligible in the absence of DHFR, or when methotrexate (MTX)—a potent inhibitor of the enzyme—is present (10 µM). Hence, the formation of the secondary product, DNP-PC, is therefore linked to the presence of the DHFR.

Using this coupled reaction, proteins conferring DHFR activity can be selected by: i) linking the genes to antibodies that specifically bind the carboxylic product of DNP-PA, and ii) isolating these genes by affinity purification using an anti-DNP antibody.

This approach is demonstrated by a routine immuno assay based on the catELISA (Tawfik et al., 1993). Microtiter plates are coated with anti-rabbit immunoglobulins (Sigma, 10 µg/well) followed by rabbit polyclonal serum that specifically bind glutaric acid derivatives (Tawfik et al., 1993) diluted 1:500 in phosphate saline buffer+1 mg/ml BSA). The plates are rinsed and blocked with BSA. The coupled reaction mixtures described above are diluted in Tris/BSA buffer (50 mM Tris, 150 mM sodium chloride, 10 mg/ml BSA, pH 7.4) and incubated for 1 hr. The plate is rinsed and an anti-DNP antibody (mouse monoclonal SPE21.11) diluted in the same buffer (1:10,000) is added and incubated for an hour. The plate is rinsed and peroxidase labelled anti mouse antibody (Jackson) is added followed by a peroxidase substrate (BM Blue; Boehringer Mannheim). A specific signal is observed only in the coupled reactions samples that contained DHFR (in addition to $H_2F$, NADPH, YAD and DNP-PA).

Highly specific anti-carboxylic acid antibodies (Tawfik et al., 1993) are used for selection in two formats.

In the first, the anti-carboxylic acid antibody is coupled chemically to a high molecular weight avidin (or streptavidin) containing complex such as that described in Example 5. Biotinylated DNA encoding DHFR is coupled to this complex via the avidin-biotin interaction as described in Example 5. This complex is then used in a compartmentalised coupled transcription/translation system which also contains YAD and a tagged YAD substrate such as DNP-PA. If there is DHFR activity in the compartment the DNP-PA is converted to DNP-PC. The anti-carboxylic acid antibodies, coupled to the DNA via the high molecular weight complex will capture only DNP-PC molecules and not aldehyde molecules. DNA from those compartments containing active DHFR (and hence encoding active DHFR if there is only one molecule of DNA per compartment) are then affinity purified by using anti-DNP antibodies.

In the second format, multiple streptavidin molecules are coupled together in a high molecular weight complex which can easily be coupled to biotinylated DNA encoding DHFR (see Example 5). This complex is used in a compartmentalised coupled transcription/translation system which also contains YAD and a YAD substrate such as MeNPOC-biotin-benzaldehyde. The biotin group in MeNPOC-biotin-benzaldehyde is "caged" (Sundberg et al., 1995; Pirrung and Huang, 1996), that is, it cannot be bound by avidin or streptavidin until a photoremovable nitrobenzyl group has been cleaved off by irradiation with light. If there is DHFR activity in the compartment the MeNPOC-biotin-benzaldehyde is converted to MeNPOC-biotin-benzoic acid. After the compartmentalised reaction has run for a while the reaction is irradiated with light and the nitrobenzyl group removed and the compound will bind to the streptavidin-DNA complex. DNA in those compartments containing active DHFR (and hence encoding active DHFR if there is only one molecule of DNA per compartment) is complexed with biotin-benzoic acid (instead of biotin-benzaldehyde) and can be affinity purified using immobilised anti-benzoic acid antibodies.

The presence of other enzymes which can catalyse the oxidation NAD$^+$ or NADP$^+$ to NADH or NADPH in the in vitro transcription/translation system can under certain circumstances make it difficult to use this YAD system for selection directly in the compartmentalised in vitro transcription/translation system. In this case the selection is carried out using the two-step compartmentalisation system described earlier. That is, the DHFR is first translated in compartments and then linked to the DNA in the same compartment by means of a suitable affinity tag. The emulsion is broken, the contents of the compartments pooled and the DNA affinity purified away from the other components of the transcription/translation system (including contaminating oxido-reductases), by using antibodies specific to a digoxigenin 'tag' attached to one end of the DNA molecule. The purified DNA molecules, together with the attached DHFR protein are then put into a reaction mixture contained the substrates for DHFR-NADPH (50 µM) and 7-8-dihydrofolate (H$_2$F; 50 µM), YAD (Sigma, 0.5 unit) and DNP-PA (50 µM) in buffer pH 7.7 (100 mM imidazole, 5 mM β-mercaptoethanol and 25 mM KCl) and the reaction re-compartmentalised by emulsification to give only one, or at most a few, molecules of DNA per compartment. Anti-carboxylic acid antibodies (Tawfik et al., 1993) are used for selection in either of the two formats described above.

Example 9

Methylation of Genetic Elements by Gene Products

DNA methyltransferases, produced by in vitro transcription/translation in the aqueous compartments of a water-in-oil emulsion, methylate the DNA molecules which encode them in the compartments.

Selecting proteins with binding or catalytic activities using the compartmentalisation system described here presents two basic requirements: i) a single molecule of DNA (or at most a few molecules) encoding the proteins to be selected is expressed in a biologically active form by a coupled transcription/translation system in the aqueous compartments of a water-in-oil emulsion; and, ii) the protein to be selected must be able to modify the genetic element that encoded it in such a way as to make it selectable in a subsequent step. In this Example, we describe a group of proteins—DNA methyl transferases (type II)—that are produced efficiently in the aqueous compartments of a water-in-oil emulsion system using a coupled transcription/translation system. Furthermore, the in vitro translated DNA methyltransferases efficiently modify the DNA molecules which encode them in situ in the aqueous compartments so that they can be selected and amplified. The target sites on the DNA molecules are modified by methylation of a cytosine at the C5 position which renders the sites resistant to cleavage by the cognate restriction endonuclease (i.e. HhaI for M.HhaI, and HaeIII for M.HaeIII). Hence, methylated DNA is selectable over non-methylated DNA by virtue of its resistance to restriction endonuclease cleavage.

The gene encoding M.HhaI is amplified by PCR using oligonucleotides HhaI-Fo2S and HhaI-Bc directly from *Haemophilus parahaemolyticus* (ATCC 10014). The gene encoding M.HaeIII is amplified by PCR using oligonucleotides HaeIII-Fo2s and HaeIII-Bc (SEQ. ID. No. 4) directly from *Haemophilus influenzae* (biogroup *aegyptius*) (ATCC 11116). Both PCR fragments are cloned into the vector pGEM-4Z (Promega) digested with HindIII and KpnI downstream of the lac promoter and T7 RNA polymerase promoter. The oligonucleotides HhaI-Bc and HaeIII-Bc (SEQ. ID. No. 4) append the efficient phage T7 gene 10 translational start site upstream of the methyltransferase gene start codon. Oligonucleotide HhaI-Fo appends an HhaI methylation/restriction site (M/R) and a HaeIII (/NotI) site to function as substrates for M.HhaI and M.HaeIII respectively. Oligonucleotide HaeIII-Fo appends a NotI/HaeIII M/R site which functions as a substrate for M.HaeIII (the M.HaeIII gene already contains two internal HhaI M/R sites). DNA sequencing identifies clones with the correct nucleotide sequence.

The pGEM-M.HhaI and pGEM-M.HaeIII plasmids described above are amplified by PCR using primers LMB2-Biotin (SEQ. ID. No. 9) and LMB3-DIG (SEQ. ID. NO. 10) as above to create either 1167 base pair DIG-M.HhaI-Biotin or a 1171 base pair DIG-M.HaeIII-Biotin DNA fragment, labelled at one end by biotin and the other end by digoxigenin, and which carry the T7 RNA polymerase promoter, the phage T7 gene 10 translational start site, the methyltransferase gene and M/R sites of HaeIII and HhaI. The PCR fragments are each purified directly using Wizard PCR Preps (Promega).

The genes required for the coupled in vitro transcription-translation of M.EcoRI and, M.EcoRV are amplified by PCR using plasmids pMB1 (Betlach et al., 1976) and pLB1 (Bougueleret et al., 1984) respectively, as templates, a back primer appending the phage T7 gene 10 translational start site and LMB3 upstream of the methyltransferase gene ribosome binding site (EcoRI-Bc or EcoRV-Bc) and a forward primer (EcoRI-Fo or EcoRI-Fo) appending LMB2. These fragments are further amplified by PCR using primers LMB2-Biotin (SEQ. ID. No. 9) and LMB3-DIG (SEQ. ID. NO. 10) as described above to create the DIG-M.Eco RI-Biotin and DIG-M.EcoRV-Biotin DNA fragments which carry the T7 RNA polymerase promoter, the phage T7 gene 10 translational start site, the methyltransferase gene and M/R sites of EcoRI and EcoRV. These PCR fragments are each purified directly using Wizard PCR Preps (Promega).

The PCR-amplified DNA-methylases genes described above are expressed in a prokaryotic in vitro coupled transcription/translation system designed for linear templates (Lesley et al., 1991). A commercial preparation of this system is used (*E. coli* S30 Extract System for Linear Templates; Promega) supplemented with T7 RNA polymerase and S-adenosyl methionine (SAM) at 80 µM concentration.

Methylation is assayed by measuring the resistance of DNA fragments labelled with DIG and biotin to cleavage by the cognate restriction enzyme using the Boehringer-Mannheim DIG-Biotin ELISA or with radioactively labelled DNA fragments and streptavidin coated magnetic beads. In vitro reaction mixtures containing DIG-Biotin labelled fragments reacted in situ by coupled in vitro transcription-translation as described below are diluted in 1×W&B buffer (1M NaCl, 10 mM Tris, 1 mM EDTA, pH 7.4)+0.1% Tween-20 (the concentration of the DIG/Biotin labelled DNA in the assay is in the range of 0-250 pM) and incubated in streptavidin coated microtiter plates (high capacity) for 30-60 mins. The plate is rinsed (3 times 2×W&B and finally with 50 mM Tris pH 7.4+5 mM MgCl$_2$) and the restriction enzymes (NEB) are added (10-50 units enzyme in 0.2 ml of the corresponding buffer) and incubated at 37° for 3-12 hrs. The plate is rinsed and peroxidase-linked anti-DIG antibodies (diluted 1:1,500 in PBS+0.1% Tween-20+2 mg/ml BSA) are added for 40-60 min followed by the peroxidase substrate (BM Blue; 70 µl/well). The absorbance (at 450 minus 650 nm) is measured after quenching with 0.5M $H_2SO_4$ (130 µl/well).

For the radioactive assay, the plasmids and PCR fragments described above are amplified by PCR using primers LMB2-Biotin (SEQ. ID. No. 9) and LMB3 and $\alpha$-$P^{32}$-CTP to give $P^{32}$-labelled DNA fragments labelled at one end by biotin and which carry the T7 RNA polymerase promoter, the phage T7 gene 10 translational start site, the methyltransferase gene and the relevant M/R sites. These PCR fragments are purified directly using Wizard PCR Preps (Promega). Reaction mixtures containing the Biotin-$P^{32}$-labelled DNA reacted in situ by coupled in vitro transcription-translation are diluted in 1×W&B buffer+0.1% Tween-20 and incubated with streptavidin coated magnetic beads (Dynal, M-280; 1-5×$10^6$ beads) for 30-60 mins. The beads are separated and rinsed (3 times 2×W&B+0.1% Tween-20+3% BSA and finally with 50 mM Tris pH 7.4+5 mM $MgCl_2$). The restriction enzymes (NEB) are added (10-50 units enzyme in 50-150 µl of the corresponding buffer) and incubated at 37° for 5-20 hrs. The supernatant is removed and the beads rinsed and resuspended in 100 µl water. The amount of radioactively-labelled DNA on the beads and in the supernatants is determined by scintillation.

All four methylases described here—M.HaeIII, M.HhaI, M.EcoRI and M.EcoRV—are expressed and active in the in vitro coupled transcription/translation. Furthermore, the in vitro translated methylase can methylate its own gene thus rendering it resistant to cleavage by the cognate methylase (self-methylation). Both processes, the coupled in vitro transcription-translation of the methylase gene as well as its methylation proceed efficiently in the same reaction mixture. More specifically, DNA fragments (at 0.5 to 10 nM concentrations) which carry the T7 RNA polymerase promoter, the phage T7 gene 10 translational start site, a methyltransferase gene and M/R sites of all four methylases become resistant to cleavage by the cognate restriction endonuclease. For example, the DNA fragment encoding M.EcoRI methyltransferase becomes resistant to cleavage by EcoRI (75-100% after 20-90 minutes at 25° C.) when incubated with *E. coli* S30 Extract System for Linear Templates (Promega), SAM (80 µM) and T7 RNA polymerase. The resistance to cleavage as a result of methylation is selective and specific: under the same conditions, resistance to cleavage by HhaI or M.EcoRV is not observed; moreover, resistance to cleavage by EcoRI is not observed when translation is inhibited (e.g. in the presence of puromycin or in the absence of T7 RNA polymerase). Similar results where obtained when survival of the genes is assayed by DIG-Biotin ELISA or with Biotin-$P^{32}$-labelled DNA fragments as described above. Methylation in trans, i.e., of DNA fragments (other than those encoding for the cognate methylase) appending M/R sites is also observed in the *E. coli* S30 coupled in vitro transcription-translation system in the presence of a gene encoding for a methylase.

Both processes, the coupled in vitro transcription-translation of the methylase genes as well as their self-methylation proceed efficiently in the aqueous compartments of a water-in-oil emulsion. More specifically, DNA fragments (at 0.1-10 nM concentrations) which carry the T7 RNA polymerase promoter, the phage T7 gene 10 translational start site, the methyltransferase gene (for example, M.HhaI) and the M/R sites of HaeIII, HhaI and EcoRI are added to *E. coli* S30 Extract System for Linear Templates (Promega) in the presence of SAM (80 µM) and T7 RNA polymerase. The ice cooled reaction mixtures are emulsified by homogenising for 1 minute with an Ultra-Turrax T25 disperser at 20,000 rpm as described in Example 1 and incubated at 25°-30° for 0-180 mins. The reaction is stopped and the aqueous phase is separated (see Example 1) and the methylation of the DIG-Biotin or Biotin-$P^{32}$-labelled DNA fragments is assayed as described above. Methylation of up to 20% of the compartmentalised genes to cleavage by HaeIII is observed after 60-180 mins incubation. No resistance is observed when the ice-cold emulsion is broken just after it is made and the reaction quenched by ether extraction ('0 mins'). The methylation is selective: under the same conditions, resistance to cleavage by HaeIII or EcoRI is not observed. Moreover, the assay of $P^{32}$-labelled DNA fragments has shown that self-methylation of both M.HaeIII and M.HhaI proceed at concentrations of genes that correspond to an average of less than one gene per compartment (0.1-0.5 nM; see Example 4). Thus, the coupled in vitro transcription-translation of the methylases genes as well as their self-methylation proceed efficiently even when only a single genetic element is present in aqueous compartments of the water-in-oil emulsion.

HaeIII methylase activity resulting from coupled transcription/translation of M.HaeIII genes is also measured in the larger microcapsules produced by stirring alone, and by stirring followed by further homogenisation with an Ultra-Turrax T25 disperser at 8,000 rpm, 9,000 rpm, or 13,500 rpm for 1 minute as described in Example 1. The results are presented in FIG. 2*b*. The concentration of M.HaeIII genes used (2.5 nM) gives an average of 1, 1.5 and 4.8 genetic elements per droplet in the emulsions homogenised at 13,500 rpm, 9,500 rpm and 8,000 rpm, respectively, and an average of 14 genetic elements per droplet in the emulsion prepared by stirring only. The addition of an anionic surfactant—e.g., sodium deoxycholate, typically to 0.5% (w/v), to the in vitro translation mixture significantly increases the percentage of genetic elements methylated in the emulsions.

Example 10

Genetic Elements Encoding DNA Methyltransferases Can be Selected and Amplified Following Their Self-methylation in the Aqueous Compartments of a Water-in-oil Emulsion.

The methylation of genes encoding for DNA-methylases allows them to be isolated and amplified in a subsequent step. The methylated DNA is selectable over non-methylated DNA by virtue of its resistance to restriction endonuclease cleavage. Thus, the genetic elements that remain intact after treatment with the cognate restriction enzyme can be amplified by PCR. However, such a selection is obviously unattainable if other genes that contain the same R/M site but do not encode for the methylase are present in same reaction mixture. This is because cross-methylation of the non-methylase genes (that are present at a large excess) will render them resistant to cleavage by the cognate restriction enzyme and thus amplifiable by PCR. Under these conditions, selection of genes encoding the methylase will become possible only if they are compartmentalised—namely, if only one, or few genes are present in a single compartment so that self methylation is the major process in that compartment. Cross-methylation is avoided since non-methylase genes that are present in compartments that do not contain a methylase gene will remain un-methylated.

Figure 1B:
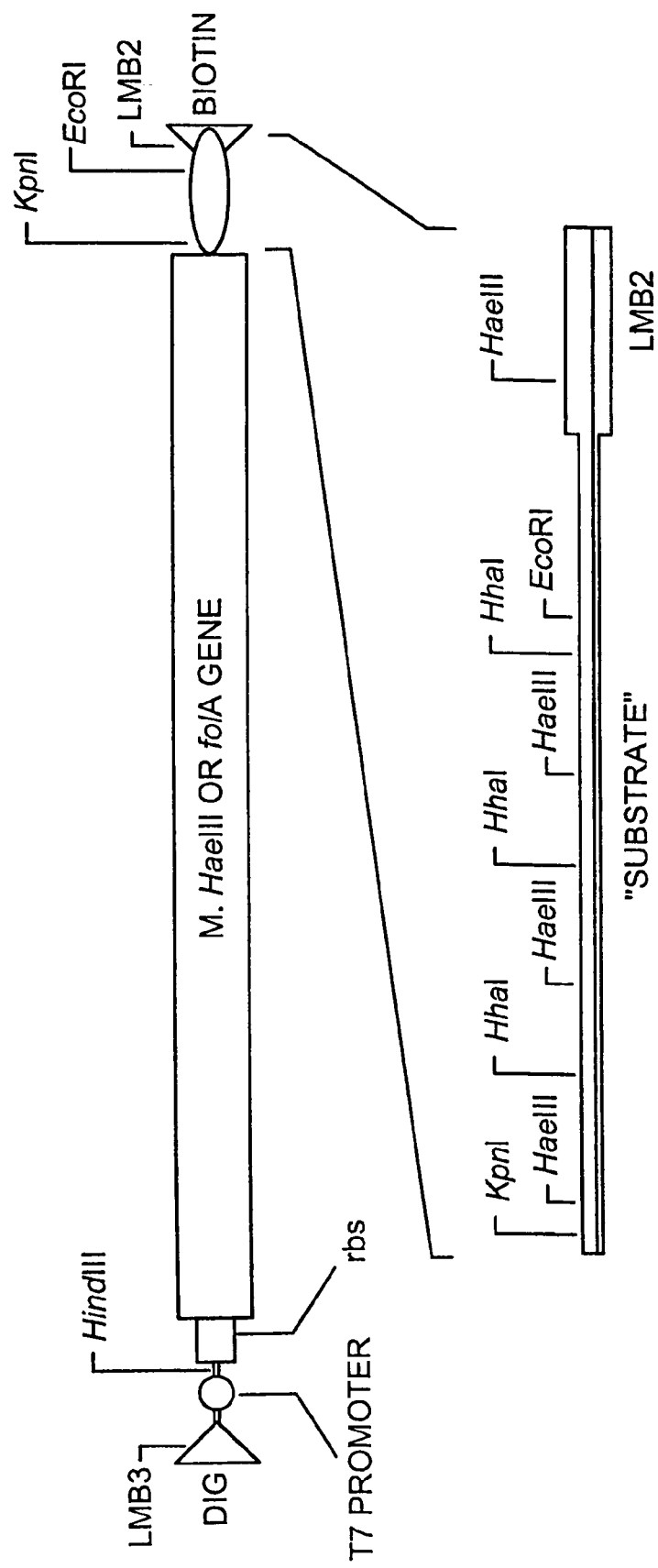

The genes used in the experiment are a 1194 base pair M.HaeIII fragment (DIG-M.HaeIII-3s-Biotin) encoding methylase HaeIII and a 681 base pair folA fragment (DIG-folA-3s-Biotin) encoding the enzyme dihydrofolate reductase (DHFR) containing additional HaeIII and HhaI restriction/modification sites (See FIG. 1*b*). Both DNA fragments are labelled at one end with digoxigenin (DIG) and the other with biotin, and contain a T7 RNA polymerase promoter (T7 Promoter) and T7 gene 10 translational initiation site (rbs) for expression in vitro.

pGEM-4Z-3s is created by annealing oligonucleotides HaeHha-P1 and HaeHha-Mi (SEQ. ID. No. 2) (Table 1) and ligating them into HindIII and EcoRI cut pGEM-4Z (Promega). The M.HaeIII gene is amplified by PCR from *Haemophilus influenzae* (biogroup *aegyptius*) (ATCC 11116) using oligonucleotides HaeIII-FoNC (SEQ. ID. No. 3) and HaeIII-Bc (SEQ. ID. No. 4) (Table 1). The folA gene is amplified from *Escherichia coli* using primers EDHFR-Fo (SEQ. ID. No. 5) and EDHFR-Ba (SEQ. ID. No. 6) (Table 1). Both amplified genes are digested with HindIII and KpnI and cloned into pGEM-4Z-3s, creating the expression vectors pGEM-HaeIII-3s and pGEM-folA-3s. DIG-M.HaeIII-3s-Biotin and DIG-folA-3s-Biotin (see FIG. 1b) are amplified from these vectors by PCR with Pfu polymerase using primers LMB2-Biotin (SEQ. ID. No. 9) and LMB3-DIG (SEQ. ID. NO. 10) (20 cycles) and purified using Wizard PCR Preps (Promega). DIG-D1.3-Biotin, a 942 bp DNA fragment containing four HaeIII R/M sites used as a substrate to assay HaeIII methylase activity, is amplified from a pUC19 derivative containing a D1.3 single-chain Fv gene (McCafferty et al., 1990) as above. A 558 bp carrier DNA (g3 carrier DNA; an internal fragment of phage fd gene III which has no T7 promoter, HaeIII or HhaI R/M sites) is amplified by PCR with Taq polymerase from pHEN1 DNA (Hoogenboom et al., 1991) using primers G3FRAG-Fo (SEQ. ID. No. 11) and G3FRAG-Ba (SEQ. ID. No. 12) (table 1) and purified by phenol-chloroform extraction and ethanol precipitation. This DNA (at ≧10 nM) was used as a carrier in dilution of all DNA used for the reactions in this example.

FIG. 3 demonstrates the selection of M.HaeIII genes encoding the DNA methylase HaeIII from an excess of folA genes (encoding DHFR which does not methylate DNA). Both genes have the same HaeIII R/M sequences appended to act as a substrate (FIG. 1b). After translation in the aqueous compartments of an emulsion the HaeIII R/M sequences attached to methylase genes are methylated. These genes are rendered resistant to cleavage by HaeIII endonuclease and are subsequently amplified by PCR. folA genes, present in other compartments, remain unmethylated, are cleaved and not amplified. The PCR products are analysed by agarose gel electrophoresis where enrichment for the M.HaeIII genes can be visualised by the appearance of a 1194 bp band (FIG. 3).

The *E. coli* S30 extract system for linear DNA (Promega) is used, supplemented with g3 carrier DNA (10 nM), DNA fragments (DIG-M.HaeIII-3s-Biotin and DIG-MfolA-3s-Biotin at ratios and concentrations indicated below), T7 RNA polymerase ($10^4$ units), sodium deoxycholate (Fluka, 0.5% w/v; in emulsified reactions only) and S-adenosyl methionine (NEB, 80 µM). Reactions are set up using DNA fragments DIG-M.HaeIII-3s-Biotin and DIG-MfolA-3s-Biotin at a ratio of $1:10^3$ and at a total concentration of 200 pM (FIG. 3A) and ratios of $1:10^4$ to $1:10^7$ and a total concentration of 500 pM (FIG. 3B). Fifty microliter reactions are prepared on ice and emulsified by stirring only as described in Example 1. Reactions are incubated for 2 hours at 25° C. To recover the reaction mixtures, the emulsions are spun at 3,000 g for 5 minutes and the oil phase removed leaving the concentrated emulsion at the bottom of the vial. Quenching buffer (0.2 ml of 25 µg/ml yeast RNA in W+B buffer: 1 M NaCl, 10 mM Tris-HCl, 1 mM EDTA pH 7.4) and 2 ml of water-saturated ether are added and the mixture is vortexed, centrifuged briefly, and the ether phase removed. The aqueous phase is washed with ether and dried (5 minutes in a Speedvac at ambient temperature). DNA is captured on 100 µg M-280 streptavidin DYNABEADS (superparamagnetic particles; Dynal; 2 hours at ambient temperature). The DYNABEADS are washed sequentially with: W+B buffer; 2.25 M Guanidine-HCl, 25 mM Tris-HCl, pH 7.4; W+B buffer; and, twice with restriction buffer. Beads are resuspended in 100 µl restriction buffer containing 10 units HaeIII (or HhaI) and incubated at 37° C. for 5 hours. The beads are washed three times with W+B buffer, twice with 50 mM KCl, 10 mM Tris-HCl, 0.1% Triton X-100, pH 9.0, and then resuspended in 100 µl of the same buffer supplemented with 1.5 mM $MgCl_2$ (PCR buffer). Aliquots of beads (2-20 µl) are amplified by PCR using Taq polymerase added at 94° C. with primers LMB2-Biotin and LMB3-DIG (50 µl reactions; 32 cycles of 1 minute at 94°, 1 minute at 55°, 2 minutes at 72°). This DNA is purified using Wizard PCR Preps and used for the second round of selection (20 pM in the 1: $10^4$ and $1:10^5$ selections and 500 pM in the $1:10^6$ and $1:10^7$ selections). For gel electrophoresis and activity assays this DNA (diluted to ~1 pM) is further amplified with primers LMB2-Nest and LMB3-Nest which anneal immediately inside LMB2 and LMB3 respectively (25 cycles of 1 minute at 94°, 1 minute at 50°, 1.5 minutes at 72°) and purified as above. This DNA (at 10 nM), which has neither DIG nor Biotin appended, is also translated in vitro in the presence of 10 nM DIG-D1.3-Biotin, a 942 bp DNA containing four HaeIII R/M sites. Methylation of the DIG-D1.3-Biotin substrate is determined by DIG-Biotin ELISA as Example 9.

Figure 3A:
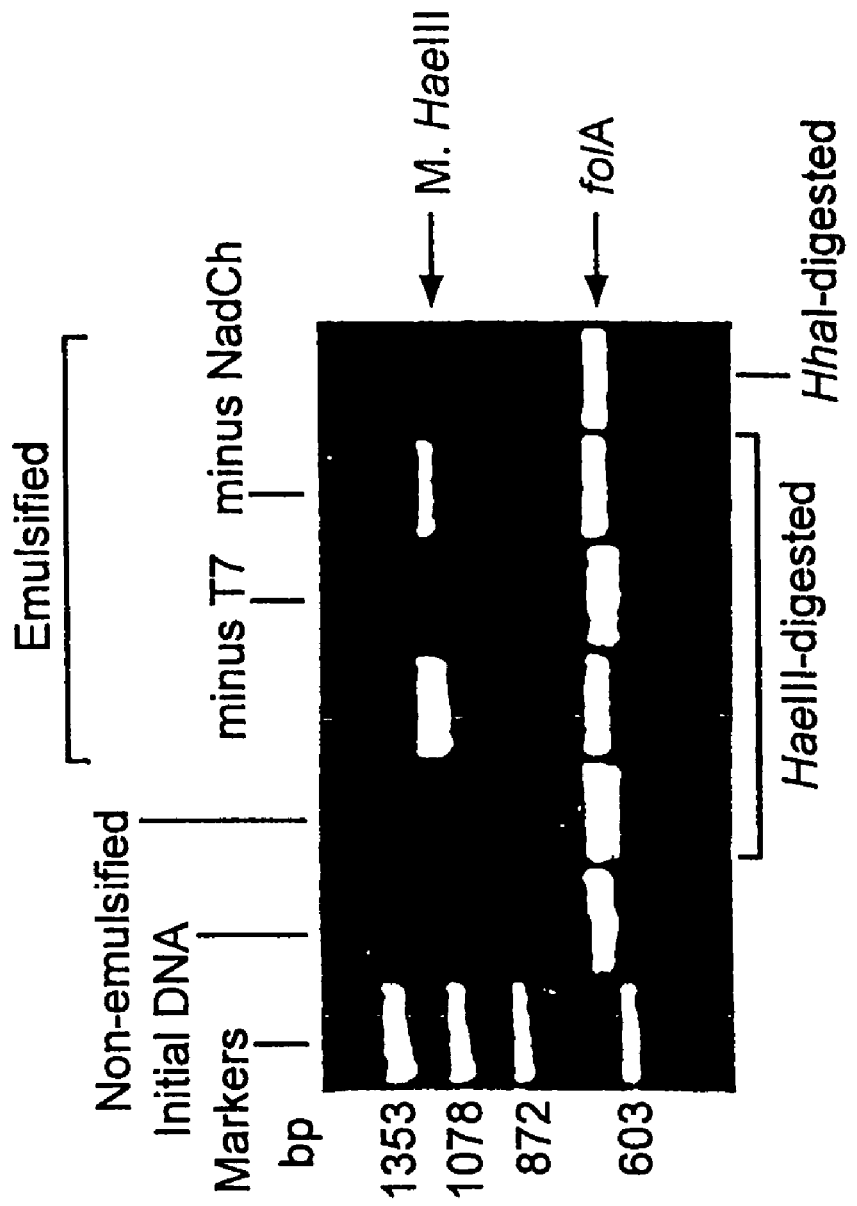
Figure 3B:
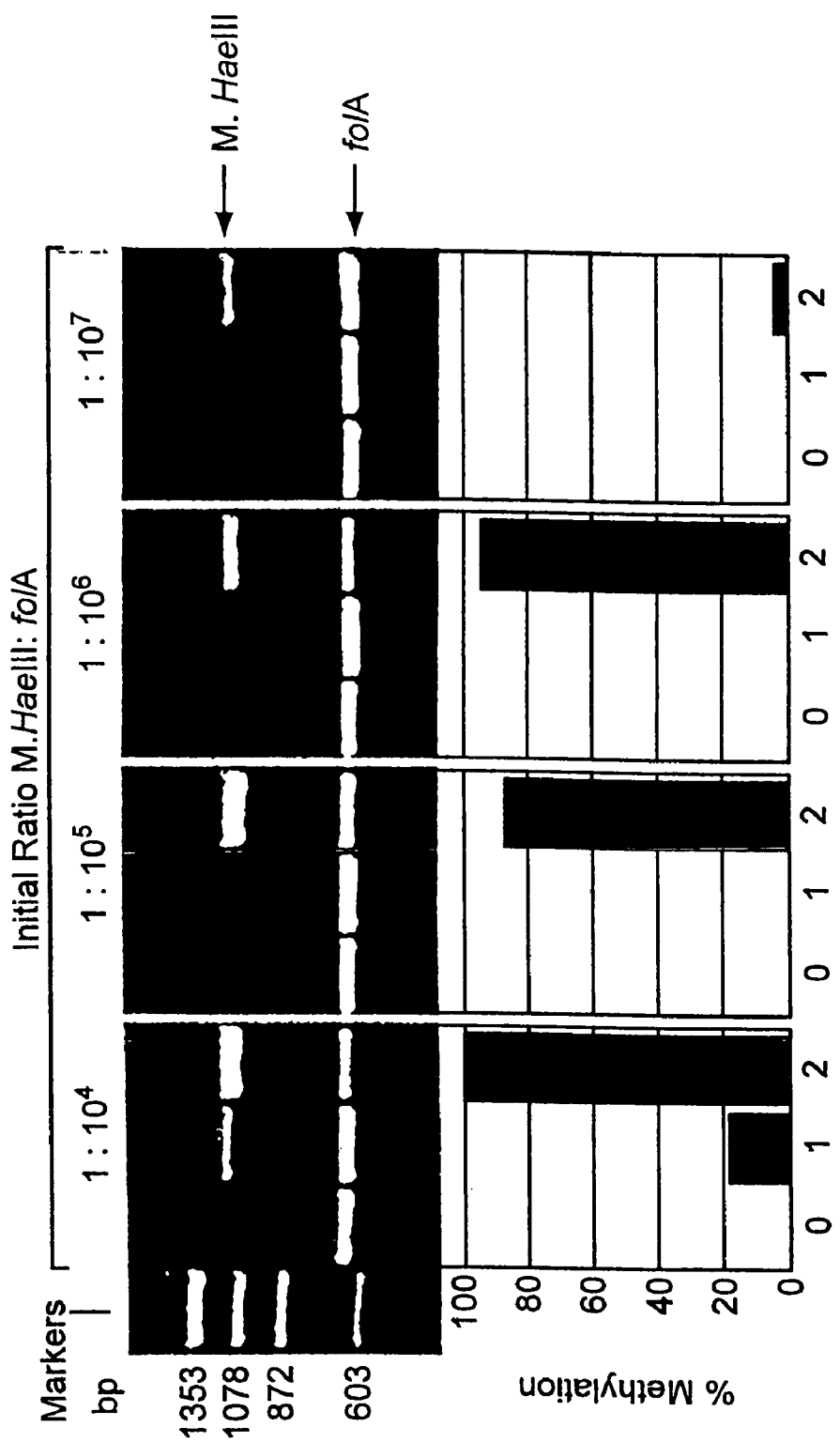

A single round of selection of a 1:1000 ratio of M.HaeIII: folA genes in the emulsion results in a roughly 1:1 final gene ratio (FIG. 3a). Several control experiments indicate that selection proceeds according to the mechanism described above: a band corresponding to the M.HaeIII gene is not observed when the initial mixture of genes is amplified by PCR; nor after reaction in solution (non-emulsified); nor when emulsified in the absence of transcription/translation (when T7 RNA polymerase is omitted); nor when the reacted genes are cleaved at R/M sites other than those of HaeIII—e.g., after digestion with HhaI. The yield of M.HaeIII DNA after selection is less than 100% primarily due to incomplete digestion by HaeIII rather than cross-methylation as indicated by the large folA band observed in the absence of methylase activity (when T7 polymerase is not added). During digestion, the concentration of DNA drops well below the $K_M$ of HaeIII (6 nM) and digestion becomes extremely inefficient.

A band corresponding to M.HaeIII genes also becomes visible after a single-round of selection starting from M.HaeIII:folA ratios of 1: $10^4$ to $1:10^5$ (FIG. 3b), but not at lower ratios, indicating an enrichment factor of at least 5000-fold. Selection of a small number of genes from a large pool (e.g., a gene library) therefore requires further rounds of selection. When the HaeIII-digested and amplified DNA from the first round of selection is subjected to a second round of selection, a band corresponding to M.HaeIII genes also became visible from $1:10^6$ and $1:10^7$ starting ratios of M.HaeIII:folA. A second round of selection is also performed on the DNA derived from the $1:10^4$ to $1:10^5$ starting ratios of M.HaeIII:folA. This gives a further enrichment, up to a ratio of approximately 3:1 in favour of the M.HaeIII genes. Before and after each round of selection the genes are amplified, translated in vitro and reacted with a separate DNA substrate to assay for HaeIII methylase activity. These assays indicate that enrichment for the M.HaeIII genes as observed by gel electrophoresis results in a parallel increase in HaeIII methylase activity (FIG. 3b).

TABLE 1

| Oligonucleotides |
|---|

HaeHha-Pl
5'-AGC TTG CAT GCC TGC GGT ACC GGC CAT GCG CAT GGC CTA GCG CAT GCG GCC GCT AGC GCG-3' (SEQ. ID. No. 1)

HaeHha-Mi
5'-AAT TCG CGC TAG CGG CCG CAT GCG CTA GGC CAT GCG CAT GGC CGG TAC CGC AGG CAT GCA-3' (SEQ. ID. No. 2)

HaeIII-FoNC
5'-CGA GCT AGA GGT ACC TTA TTA ATT ACC TTT ACA AAT TTC CAA TGC AGA TTT TAT-3' (SEQ. ID. No. 3)

HaeIII-Bc
5'-GCA TCT GAC AAG CTT AAT AAT TTT GTT TAA CTT TAA GAA GGA GAT ATA CAT ATG AAT TTA (SEQ. ID. No. 4)
ATT AGT CTT TTT TCA GGT GCA GGG-3'

EDHFR-Fo
5'-CGA GCT AGA GGT ACC TTA TTA CCG CCG CTC CAG AAT CTC AAA GCA ATA G-3' (SEQ. ID. No. 5)

EDHFR-Ba
5'-GCA TCT GAC AAG CTT AAT AAT TTT GTT TAA CTT TAA GAA GGA GAT ATA CAT ATG ATC AGT (SEQ. ID. No. 6)
CTG ATT GCG GCG TTA GCG GTA G-3'

LMB2-Nest
5'-GAA TTG GAT TTA GGT GAC-3' (SEQ. ID. No. 7)

LMB3-Nest
5'-CAT GAT TAC GCC AAG CTC-3' (SEQ. ID. No. 8)

LMB2-Biotin
5'-Biotin-GTA AAA CGA CGG CCA GT-3' (SEQ. ID. No. 9)

LMB3-DIG
5'-Digoxigenin-CAG GAA ACA GCT ATG AC-3' (SEQ. ID. No. 10)

G3FRAG-Fo
5'-GTC TCT GAA TTT ACC GTT CCA G-3' (SEQ. ID. No. 11)

G3FRAG-Ba
5'-GAA ACT GTT GAA AGT TGT TTA G-3' (SEQ. ID. No. 12)

P2T7Ba
5'-ATT ATA ATA CGA CTC ACT ATA GGG AGA GTT ATC AGG CAT GCA CC-3' (SEQ. ID. No. 13)

P9Fo
5'-CTA GCT CCC ATT AAG GAG-3' (SEQ. ID. No. 14)

LMB2
5'-GTA AAA CGA CGG CCA GT-3' (SEQ. ID. No. 15)

LMB3
5'-CAG GAA ACA GCT ATG AC-3' (SEQ. ID. No. 16)

HhaI-Fo2S
5'-CGA GCT AGA GGT ACC GCG GCC GCT GCG CTT ATT AAT ATG GTT TGA AAT TTA ATG ATG AAC (SEQ. ID. No. 17)
CAA TG-3'

HhaI-Bc
5'-GCA TCT GAC AAG CTT AAT AAT TTT GTT TAA CTT TAA GAA GGA GAT ATA CAT ATG ATT GAA (SEQ. ID. No. 18)
ATA AAA GAT AAA CAG CTC ACA GG-3'

HaeIII-Fo2s
5'-CGA GCT AGA GGT ACC GCG GCC GCT GCG CTT ATT AAT TAC CTT TAC AAA TTT CCA ATG CAG (SEQ. ID. No. 19)
ATT TTA T-3'

EcoRI-Bc
5'-CAG GAA ACA GCT ATG ACA AGC TTA ATA CGA CTC ACT ATA GGG AGA TAT TTT TTA TTT TAA (SEQ. ID. No. 20)
TAA GGT TTT AAT TAA TGG-3'

EcoRI-Fo
5'-GTA AAA CGA CGG CCA GTG AAT TCT TAT TAC TTT TGT AAT CGT TTG TTT TTT ATC-3' (SEQ. ID. No. 21)

TABLE 1-continued

Oligonucleotides

EcoRV-Bc
5'-CAG GAA ACA GCT ATG ACA AGC TTA ATA CGA CTC ACT ATA GGG AGA AAT GGG TTT CTT TGG    (SEQ. ID. No. 22)
CAT ATT TTT TAC AAA TG-3'

EcoRV-Fo
5'-GTA AAA CGA CGG CCA GTG AAT TCG ATA TCT TAT TAC TCT TCA ATT ACC AAA ATA TCC CC-3'    (SEQ. ID. No. 23)

LMB2-Biotin has a 5'-terminal biotin linked by a 16-atom spacer arm. LMB3-DIG has a 5'-terminal digoxygenin linked by a 12-atom space arm.
Oligonucleotides labelled at the 5' terminus with Biotin or Digoxigenin were purchased from Eurogentec.

REFERENCES

Anderson, C. W., Straus, J. W. and Dudock, B. S. (1983) Methods Enzymol, 101, 635-44.

Anderson, I. E. (1993) Curr. Op. Struct. Biol., 3, 24-30.

Ash, M. and Ash, 1. (1993) Handbook of industrial surfactants. Gower, Aldershor.

Baccanari, D.P., Averett, D., Briggs, C. and Burchall, J.(1977) Biochemistry, 16, 3566- 72.

Barany, F. (1991) PCR Methods Applic., 1,5-16.

Bass, S., Greene, R. and Wells, J. A. (1990) Proteins, 8, 309-14.

Becher, P. (1957) Emulsions: theory and practice. Reinhold, New York.

Benita, S., Ed. (1996). Microencapsulation: methods and industrial applications. Drugs and pharmaceutical sciences. Edited by Swarbrick, J. New York: Marcel Dekker.

Benner, S. A. (1994) Trends Biotechnol, 12, 158-63.

Berman, J. Eisenberg, S. and Tye, B. K. (1987) Methods Enzymol, 155, 528-37.

Betlach, L., Hershfield, V., Chow, L.,Brown, W., Goodman, H. M. & Boyer, H. W. (1976). A restriction endonuclease analysis of the bacterial plasmid controlling the EcoRi restriction and modification of DNA. Federation Proceedings 35, 2037-2043.

Blattner, F. R. and Dahlberg, J. E. (1972) Nature New Biol, 237, 227-32.

Bougueleret, L., Schwarzstein, M., Tsugita, A. & Zabeau, M. (1984). Characterization of the genes coding for the Eco RV restriction and modification system of Escherichia coli. Nucleic Acids Res 12(8), 3659-76.

Bru, R. & Walde, P. (1991). Product inhibition of alpha-chymotrypsin in reverse micelles. Eur J Biochem 199(1), 95-103.

Bru, R. & Walde, P. (1993). Catalytic activity of elastase in reverse micelles. Biochem Mol Biol Int: 31(4), 685-92.

Cahill, P., Foster, K. and Mahan, D. E. (1991) Clin Chem, 37, 1482-5.

Chakrabarti, A. C., Breaker, R. R., Joyce, G. F. & Deamer, D. W. (1994). Production of RNA by a polymerase protein-encapsulated within phospholipid vesicles. J Mol Evol 39(6), 555-9.

Chamberlin, M. and Ring. J. (1973) J Biol Chem, 248, 2235-2244.

Chang, T. M. (1987). Recycling of NAD(P) by multienzyme systems immobilized by microencapsulacion in artificial cells. Methods Enzymol 136(67), 67-82.

Chang, T. M. S. (1992). Recent advances in artificial cells based on microencapsulation. In Microcapsules and nanoparticles in medicine and pharmacy (Donbrow, M., ed.), pp. 323- 339. CRC Press, Boca Raton, Fla.

Chapman, K. B. and Szostak, J. W. (1994) Curr. op. Struct. Biol., 4, 6 18-622.

Chetverin, A. B. and Spirin, A. S. (1995) Prog Nucleic Acid Res Mol Biol, 51, 225-70.

Clackson, T. and Wells, J. A. (1994) Trends Biotechnol, 12, 173-84.

Creagh, A. L., Prausnitz, J. M. & Blanch, H. W. (1993). Structural and catalytic properties of enzymes in reverse micelles. Enzyme Microb Technol 15(5), 383-92.

Cull, M. G., Miller, J. F. and Schatz, P. J. (1992) Proc Nati Acad Sci U S A, 89, 1865-9.

Dickinson, E. (1994) In Wedlock, D. J. (ed.), Emulsions and droplet size control.

Butterworth-Heine-mann, Oxford, Vol. pp. 191-257.

Ellington, A. D. and Szostak, J. W. (1990) Nature, 346, 81822.

Eliman, J., Mendel, D., Anthony, C. S., Noren, C. J. and Schultz, P. G. (1991) Methods Enzymol, 202, 301-36.

Fahy, E., Kwoh, D. Y. and Gingeras, T. R. (1991) PCR Methods Appl, 1, 25-33.

Fields, S. & Song, O. (1989) A novel genetic system to detect protein-protein interactions. Nature 340, 245-6.

Finch, C. A. (1993). Encapsulation and controlled release. Spec. Publ.-R. Soc. Chem. 138, 35.

Fisch, I., Kontermann, R. E., Finnern, R., Hartley, O., Soler, G. A., Griffiths, A. D. and Winter, G. (1996) Proc Nail Acad Sci U S A, 93, 7761-6.

Freese, E. C., (1959) J. Mol. Biol., 1, 87.

Friedberg, E. C., Walker, G. C. and Siede, W. (1995) DNA repair and mutagenesis. ASM Press, Washington D.C.

Gold, L., Polisky, B., Uhieribeck, O. and Yarus, M. (1995) Annu Rev Biochem, 64, 763- 97.

Green, R. and Szostak, J. W. (1992) Science, 258, 1910-5.

Gregoriadis, G. (1976) Methods Enzymol, 44, 21 8-27.

Griffiths, A. D., Williams, S. C., Hartley, o., Tomlinson, I. M., Waterhouse, P., Crosby, W. L., Kontermann, R. E., Jones, P. T., Low, N. M., Allison, T. J. and et a.l. (1994) Embo J, 13, 3245-60.

Haber, J., Maslakiewicz, P., Rodakiewicz, N. J. & Walde, P. (1993). Activity and spectroscopic properties of bovine liver catalase in sodium bis(2- ethylhexyl)sulfosuccinate/isooctane reverse micelles. Eur J Biochem 217(2), 567-73.

Hermanson, G. T. (1996) Bioconjugate techniques. Academic Press, San Diego.

Hochuli, E., Dobeli, H. and Schacher, A. (1987) J Chromatogr, 411, 177-84.

Hoogenboom, H. R., et al., (1991) Nucl. Acids Res., 91, 4133-4137.

Hoogenboom, H. R. (1997). Designing and optimizing library selection strategies for generating high-affinity antibodies. Trends Biotechnol. 15, 62-70.

Hoogenboom, H. R. (1997) Trends Biotechnol., 15, 62-70.

Janda, K. D., Lo, L.-C., Lo, C.-H. L., Sim, M., -M., Wang, R., Wong, C.-H. and Lerner, R.A. (1997) Science, 275, 945-948.

Johannsson, A. (1991) In Price, C. P. and Newman, D. J. (ed.), Heterogeneous enzyme immunoassays. Stockton Press, New York, Vol. pp. 295-325.

Johannsson, A. and Bates, D. L. (1988) In Kemeny, D. M. and Challacombe, S.i. (ed.)

Amplification by second enzymes. John Wiley, Chichester, Vol. pp. 85-106.

Joyce, G. F. (1994) *Curr. op. Structural Bid.,* 4, 331-336.

Kadir, F. H. and Moore, G. R. (1990) Febs Lett, 276, 81-4.

Kallen, R. G. & Jencks, W. P. (1966). The mechanism of the condensation of formaldehyde with tetrahydrofolic acid. *J. Biol. Chem.* 241, 5851-5863.

Katanaev, V. L., Kurnasov, O. V. and Spirin, A. S. (1995) Febs Lett, 359, 89-92.

Keij, J. F., Groenewegen, A. C. & Visser, J. W. M. (1994) High-speed photodamage cell sorting: An evaluation of the ZAPPER prototype. *Methods in cell biology* 42, 371-358.

Klug, A. (1995) Ann N Y Acad Sci, 758, 143-60.

Klug, A. and Schwabe, J. W. (1995) Faseb T, 9, 597-604.

Kolb, V. A., Makeyev, E. V., Kommer, A. and Spirin, A. S.(1995) Biochem Cell Biol, 73, 1217-20.

Kowalczykowski, S. C., Dixon, D. A., Eggleston, A. K., Lauder, S. D. and Rehrauer, W. M. (1994) Microbiol Rev, 58, 401-65.

Krumdiek, C. L. & Baugh, C. M. (1980) Solid-phase synthesis of pteroylpolyglutanutes.

Methods Enzymol. pp. 524-529

Kumar, A., Kumar, A. & Katiyar, S. S. (1989). Activity and kinetic characteristics of glutathione reductase in vitro in reverse micellar waterpool. *Biochim Biophys Acta* 996(1-2), 1-6.

Landegren, U., Kaiser, R., Sanders, J. and Hood, L. (1988) Science, 241, 1077-80.

Lesley, S. A., Brow, M. A. & Burgess, R. R. (1991). Use of in vitro protein synthesis from polymerase chain reaction-generated templates to study interaction of Eschericbia coli transcription factors with core RNA polymerase and for epitope mapping of monoclonal antibodies. *J Biol Chem* 266(4), 2632-8.

Lesley, S. A. (1995) Methods Mol Biol, 37, 265-78.

Lesley, S. A., Brow, M. A. and Burgess, R. R. (1991) J Biol Chem, 266, 2632-8.

Leung, D. W., Chen, E. and Goeddel, D. V. (1989) Technique, 1, 11-15.

Liao, H., McKenzie, T. and Hageman, R. (1986) Proc Nati Acad Sci U S A, 83, 576-80.

Lim, F. & Sun, A. M. (1980). Microencapsulated islets as bioartificial endocrine pancreas. *Science* 210(4472), 908-10.

Lim, F., Ed. (1984). Biomedical applications of microencapsulation. Boca Raton, Fla.: CRC Press.

Lissant, K. J., ed. Emulsions and emulsion technology. Surfactant Science New York: Marcel Dekker, 1974.

Lissant, K. J., ed. Emulsions and emulsion technology. Surfactant Science New York: Marcel Dekker, 1974.

Lissant, K. J., ed. Emulsions and emulsion technology. Surfactant Science New York: Marcel Dekker, 1984.

Low, N. M., Holliger, P. H. and Winter, G. (1996) J Mol Biol, 260, 359-68.

Lowinan, E. B., Bass, S. H., Simpson, N. and Wells, J.A. (1991) Biochemistry, 30, 10832-8.

Luisi, P. L. & B., S. -H. (1987). Activity and conformation of enzymes in reverse micellar solutions. *Methods Enzymol* 136(188), 188-216.

Ma, C., Kudlicki, W., Odom, O. W., Kramer, G. and Hardesty, B. (1993) Biochemistry, 32, 7939-45.

Magdassi, S., Frenkel, M., Carti, N. and Cazan, R. (1984) 97, 377-379.

Manley, J. L., Fire, A., Samuels, M. and Sharp, P. A. (1983) Methods Enzyniol, .101, 568-82.

Mao, Q. & Walde, P. (1991). Substrate effects on the enzymatic activity of alpha- chymotrypsin in reverse micelles. *Biochern Biophys Res Commun* 178(3). 1105-12.

Mao, Q., Walde, P. & Luisi, P. L. (1992). Kinetic behaviour of alpha-chymotrypsin in reverse micelles. A stopped-flow study. *Eur J Biochem* 208(1), 165-70.

Mattheakis, L. C., Bhatt, R. R. and Dower, W. J. (1994) Proc Natl Acad Sci U S A, 91, 9022-6.

McCafferty, J., Griffiths, A. D., Winter, G. and Chiswell, D. J. (1990) Nature, 348, 552-4.

Melton, D. A., Krieg, P. A., Rebagliati, M. R., Maniatis, T., Zinn, K. and Green, M. R (1984) Nucleic Acids Res, 12, 703556.

Mendel, D., Cornish, V. W. and Schultz, P. G. (1995) Annu Rev Biophys Biomol Struct, 24, 435-62.

Menger, F. M. & Yamada, K. (1979). *J. Am. Chem. Soc.* 101, 6731-6734.

Miele, E. A., Mills, D. R. and Kramer, F. R. (1983) J Mol Biol, 171, 281-95.

Mize, P. D., Hoke, R. A., Linn, C. P., Reardon, J. E. and Schulte, T. H. (1989) Anal Biochem, 179, 229-35.

Montigiani, S., Neri, G., Neri, P. and Nedi, D. (1996) J Mol Biol, 258, 6-13.

Moore, M. J. (1995) Nature, 374, 766-7.

New, R. R. C., Ed. (1990). Liposomes: a practical approach. The practical appraoch series. Edited by Rickwood, D. & Hames, B. D. Oxford: Oxford University Press.

Nissim, A., Hoogenboom, H. R. I Tomlinson, I. M., Flynn, G., Midgley, C., Lane, D. and Winter, G. (1994) Embo J, 13, 692-8.

Oberholzer, T., Albrizio, M. & Luisi, P. L. (1995a). Polymerase chain reaction in liposomes. *Chemistry and Biology* 2, 677-682.

Oberholzer, T., Wick, R., Luisi, P. L. & Biebricher, C. K. (1995b). Enzymatic RNA replication in self-reproducing vesicles: an approach to a minimal cell. *Biochem Biophys Res Commun* 207(1), 250-7.

Parmley, S. F. and Smith, G. P. (1988) Gene, 73, 305-18.

Pelhm, H. R. and Jackson, R. J. (1976) Eur J Biochem, 67, 247-56.

Perelson, A. S. and Oster, G. F. (1979) J Theor Biol. 81, 64570.

Perez, G. M., Sanchez, F. A. & Garcia, C. F. (1992). Application of active-phase plot to the kinetic analysis of lipoxygenase in reverse micelles. *Biochem J.*

Pirrung, M. C. and Huang, C. Y. (1996) Bioconjug Chem, 7, 31721.

Posner, B. A., Li, L., Bethell, R., Tsuji, T. and Benkovic, S. J. (1996) Biochemistry, 35, 1653-63.

Roberts, B. E., Gorecki, M., Mulligan, R. C., Danna, K. J., Rozenblatt, S. and Rich, A. (1975) Proc Nati Acad Sci U S A, 72, 1922-6.

Roberts, J. W. (1969) Nature, 224, 1168-74.

Roberts, R. & Szostak, J. (1997) RNA-peptide fusions for the in vitro selection of peptides and proteins. *Proc Nati Acad Sci USA* 94, 12297-12302.

Rosenberg, M., Weissman, S. and decrombrugghe, B. (1975) J Biol Chem, 250, 4755-64.
Saiki, R. K., Gelfand, D. H., Stoffel, S., Scharf, S. J., Higuchi, R., Horn, G. T., Mullis, K. B. and Erlich, H. A. (1988) Science, 239, 487-91.
Sambrook, J., Fritsch, E. F. and Maniatis, T. (1989) Molecular cloning: a laboratory manual. Cold Spring Harbor Laboratory Press, New York.
Savage, M. D., Mattson, G., Desai, S., Nielander, G. W., Morgensen, S. and Conklin, E. J. (1994) Avidin-biotin chemistry: a handbook. Pierce Chemical Company, Rockford.
Schick, M. J. (1966) Nonionic surfactants. Marcel Dekker, New York.
Sherman, P. (1968) Emulsion science. Academic Press, London.
Smith, G.P. (1985) Science, 228, 1315-7.
Soumillion, P., Jaspers, L., Bouchet, M., Marchand, B. J., Winter, G. and Fastrez, J. (1994) J Mol Biol, 237, 415-22.
Stemmer, W. P. (1994a) Nature, 370, 389-91.
Stemmer, W. P. (1994b) Proc Nati Acad Sci U S A, 91, 10747-51.
Stofko, H. R., Cart, D. W. and Scott, J. D. (1992) Febs Lett, 302, 274-8.
Sun, A. M., Vasek, I. & Tai, I. (1992). Microencapsulation of living cells and tissues. In *Microencapsulation and nanoparticles in medicine and pharmacy* (Donbrow, M., ed.), pp. 315-322. CRC Press, Boca Raton, Fla.
Sundberg, S. A., Barrett, R. W., Pirrung, M., Lu, A. L., Kiangsoontra, B. and Holmes, C. P. (1995) J. Am. CheM. Soc., 117, 12050-12057.
Tawfik, D. S., Green, B. S., Chap, R., Sela, M. & Eshhar, Z. (1993). catELISA: a facile general route to catalytic antibodies. *Proc Nan Acad Sci U S A* 90(2), 373-7.
Tokatlidis, K., Friguet, B., Deville, B. D., Baleux, F., Fedorov, A. N., Navon, A.,
Djavadi, O. L. and Goldberg, M. E. (1995) Philos Trans R Soc Land B Biol Sci, 348, 89- 95.
Tripet, B., Yu, L., Bautista, D. L., Wang, W. Y., Irvin, R. T. and Hodges, R. S. (1996) Protein Engng., 9, 1029-1042.
Tuerk, C. and Gold, L. (1990) Science, 249, 505-10.
van Hal, D. A., Bouwstra, J. A. & Junginger, H. E. (1996). Nonioaic surfactant vesicles containing estradiol for topical application. In *Microencapsulation: methods and industrial applications* (Benita, S., ed.), pp. 329-347. Marcel Dekker, New York.
Walde, P., Goto, A., Monnard, P.-A., Wessicicen, M. & Luisi, P. L. (1994). Oparin's reactions revisited: enzymatic synthesis of poly(adenylic acid) in micelles and self- reproducing vesicles. *J. Am. Chem. Soc.* 116, 7541-7547.
Walde, P., Han, D. & Luisi, P. L. (1993). Spectroscopic and kinetic studies of lipases solubilized in reverse inicelles. *Biochemistry* 32(15), 4029-34.
Walde, P., Peng, Q., Fadnavis, N. W., Battistel, E. & Luisi, P. L. (1988). Structure and activity of trypsin in reverse inicelles. *Eur J Biochem* 173(2), 401-9.
Walker, GT., Fraiser, M.S., Schram, J.L., Little, M.C., Nadeau, 1G. and Malinowski, D. P. (1992) Nucleic Acids Res, 20, 1691-6.
Weil, P. A., Luse, D. S., Segall, J. and Roeder, R. G. (1979) Cell, 18, 469-84.
Whateley, T. L. (1996). Microcapsules: preparation by interfacial polyinerisation and interfacial complexation and their applications. In *Microencapszdation: methods and industrial applications* (Benita, S., ed.), pp. 349-375. Marcel Dekker, New York.
Wick, R. & Luisi, P. L. (1996). Enzyme-containing liposomes can endogenously produce membrane-constituting lipids. *Chem Biol* 3(4), 277-85.
Widersten, M. and Mannervik,. B: (1995) J Mol Biol, 250, 115-22.
Williams, J. W., Morrison, J. F. and Duggleby, R. G. (1979) Biochemistry, 18, 2567-73;
Winter, G., Griffiths, A. D., Hawkins, R. E. and Hoogenboom, H. R. (1994) Annu Rev Immunol, 12, 433-55.
Wyatt, J. R.1 Chastain, M. and Puglisi, J. D. (1991) Biotechniques, 11, 764-9.
Yaxnagishi, J., Kawashima, H., Matsuo, N., Ohue, M., Yamayoshi, M., Fukui, T.,
Kotani, H., Furuta, R., Nakano, K. and Yamada, M. (1990) Protein Eng, 3, 713-9.
Yelamos, J., Klix, N., Goyenechea, B., Lozano, F., Chui, Y. L., Gonzalez, F. A., Pannell,. R., Neuberger, M. S. and Milstein, C. (1995) Nature, 376, 225-9.
Zaccolo, M., Williams, D. M., Brown, D. M. and Gherardi, E. (1996) J Mol Biol, 255, 589-603.
Zakrwwski, S. F. (1980) Preparation of tritiated dihydrofolic acid of high specific activity. Methods Enzymol. pp.539-.
Zaug, A. J. and Cech, T. R. (1986) Biochemistry, 25, 4478-82.
Zaug, A. J. and Cech, T. R. (1986) Science, 231, 470-5.
Zaug, A. J., Been, M. D. and Cech, T. R. (1986) Nature, 324, 429-33.
Zubay, G. (1973) Annu Rev Genet, 7, 267-87.
Zubay, G. (1980) Methods Enzymol, 65, 856-77.

The invention claimed is

1. A method for increasing the concentration of a nucleic acid molecule by polymerase chain reaction amplification comprising the steps of:
   (a) forming aqueous microcapsules from a thermostable water-in-oil emulsion, wherein a plurality of the microcapsules include a nucleic acid molecule, a bead, and an aqueous solution comprising components necessary for polymerase chain reaction amplification;
   (b) amplifying the nucleic acid molecule in the microcapsules to form amplified copies of the nucleic acid molecule which bind to said bead; and
   (c) breaking the microcapsules and selecting for said amplified copies of the nucleic acid molecule using a tag, wherein the tag comprises one member of a binding pair.

2. The method of claim 1 wherein the emulsion includes at least one emulsion stabilizer.

3. The method of claim 2 wherein the emulsion stabilizer is a non-ionic surfactant.

4. The method of claim 3 wherein the emulsion stabilizer is selected from the group consisting of sorbitan monooleate and polyoxyethylenesorbitan monooleate.

5. The method of claim 2 wherein the emulsion stabilizer is an anionic surfactant.

6. The method of claim 5 wherein the emulsion stabilizer is selected from the group consisting of sodium cholate, sodium glycocholate, sodium taurocholate, and sodium deoxycholate.

7. The method of claim 1 wherein the nucleic acid molecule comprises a biotin tag.

8. The method of claim 1 wherein the bead is selected from the group consisting of polystyrene and magnetic beads.

9. The method of claim 1 wherein a plurality of microcapsules when formed contains on average one or less than one nucleic acid molecule per microcapsule.

10. The method of claim 1 wherein a plurality of microcapsules when formed each contains on average between 5 and 1000 nucleic acid molecules.

11. The method of claim 1 wherein the binding pair is biotin -avidin/streptavidin.

* * * * *